US011105819B2

United States Patent
Schellenberger et al.

(10) Patent No.: US 11,105,819 B2
(45) Date of Patent: *Aug. 31, 2021

(54) METHOD, COMPOSITION AND DEVICE FOR SAMPLING NATRIURETIC PEPTIDES IN A BIOLOGICAL FLUID

(71) Applicant: CRIMSON U.S. ASSETS LLC, Wilmington, DE (US)

(72) Inventors: Ute Schellenberger, Palo Alto, CA (US); Eric E. Niederkofler, Glendale, AZ (US); Urban A. Kiernan, Chandler, AZ (US); Jessica O'Rear, Redwood City, CA (US); Randall W. Nelson, Phoenix, AZ (US)

(73) Assignee: CRIMSON U.S. ASSETS LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,360

(22) Filed: Jan. 24, 2020

(65) Prior Publication Data

US 2020/0158739 A1    May 21, 2020

Related U.S. Application Data

(60) Continuation of application No. 15/269,423, filed on Sep. 19, 2016, now Pat. No. 10,641,781, which is a
(Continued)

(51) Int. Cl.
*G01N 33/74* (2006.01)
*G01N 1/28* (2006.01)

(52) U.S. Cl.
CPC .............. *G01N 33/74* (2013.01); *G01N 1/28* (2013.01); *G01N 2333/58* (2013.01); *G01N 2560/00* (2013.01); *Y10T 436/107497* (2015.01)

(58) Field of Classification Search
CPC combination set(s) only.
See application file for complete search history.

(56) References Cited

U.S. PATENT DOCUMENTS

| 5,786,163 A | 7/1998 | Hall |
| 6,102,872 A | 8/2000 | Doneen et al. |

(Continued)

FOREIGN PATENT DOCUMENTS

| CA | 2430889 A1 | 12/2003 |
| DE | 19628236 A1 | 1/1998 |

(Continued)

OTHER PUBLICATIONS

"Protease Inhibitor Cocktail 1", BP Biochemicals Product Catalog, Catalog No. 25,100, XP-002530773, 2004 (Retrieved from the Internet: http://bpbiochemicals.com/25,100.htm).
(Continued)

*Primary Examiner* — Rebecca M Fritchman
(74) *Attorney, Agent, or Firm* — K&L Gates LLP; Louis C. Cullman; Michelle Glasky Bergman

(57) ABSTRACT

Disclosed is a composition that synergistically prevents proteolysis or modification of peptides in sampled biological fluids using sulfonyl fluoride family protease inhibitors at high concentrations combined with at least one additional protease inhibitor of a different type, preferably a broad spectrum protease inhibitor, and a chelator. A preferred embodiment uses AEBSF at 10 mM, Benzamidine at 20 mM and EDTA as the chelator. The disclosed composition may be combined with other protease inhibitors to further modulate its specificity, for instance to additionally target acidic proteases. Additional protease inhibitors, reducing agents, stabilizers and buffering agents may be combined with the disclosed compositions in devices for sampling or testing biological fluids for levels of peptides of interest, or methods therefore. The disclosed devices, compositions and methods
(Continued)

are of particular use in sampling and testing for the level of natriuretic peptides.

19 Claims, 22 Drawing Sheets

Related U.S. Application Data division of application No. 12/038,355, filed on Feb. 27, 2008, now Pat. No. 9,482,677.

(56) References Cited

U.S. PATENT DOCUMENTS

| | | | |
|---|---|---|---|
| 6,162,902 A | 12/2000 | Mischak et al. | |
| 6,235,509 B1 | 5/2001 | Fernholz | |
| 6,783,672 B2 | 8/2004 | Tubbs et al. | |
| 6,806,075 B1 | 10/2004 | Morser et al. | |
| 6,974,704 B2 | 12/2005 | Nelson et al. | |
| 7,083,723 B2 | 8/2006 | Tubbs et al. | |
| 7,083,724 B2 | 8/2006 | Tubbs et al. | |
| 7,087,163 B2 | 8/2006 | Tubbs et al. | |
| 7,087,164 B2 | 8/2006 | Tubbs et al. | |
| 7,087,165 B2 | 8/2006 | Tubbs et al. | |
| 7,309,468 B2 | 12/2007 | Stevens et al. | |
| 7,341,838 B2 | 3/2008 | Buechler et al. | |
| 2004/0067889 A1* | 4/2004 | Belenky | A61K 35/14 514/12.4 |
| 2005/0118662 A1 | 6/2005 | Spinke et al. | |
| 2006/0110775 A1 | 5/2006 | Borgya et al. | |
| 2006/0110776 A1 | 5/2006 | Borgya et al. | |
| 2006/0160150 A1 | 7/2006 | Seilhamer et al. | |
| 2006/0183681 A1* | 8/2006 | Ebrahim | G01N 33/74 514/2.3 |
| 2007/0099241 A1 | 5/2007 | Borgya et al. | |
| 2007/0117156 A1 | 5/2007 | Borgya et al. | |

FOREIGN PATENT DOCUMENTS

| | | |
|---|---|---|
| EP | 09250526 | 8/2009 |
| JP | 2000-514299 A | 1/1998 |
| JP | 2002-506028 A | 9/1999 |
| JP | 2005-525126 A2 | 11/2003 |
| JP | 2004-29021 A | 1/2004 |
| JP | 2008-534440 A | 8/2006 |
| WO | 1989/08452 A1 | 9/1989 |
| WO | 2000/35951 | 6/2000 |
| WO | 2003/097237 A2 | 11/2003 |
| WO | 2004/099252 | 11/2004 |
| WO | 2006/088624 A2 | 8/2006 |
| WO | 2007/041645 A2 | 4/2007 |

OTHER PUBLICATIONS

Belenky et al., The effect of class-specific protease inhibitors o . . . , Clinica Chimica Acta, 2004, v:340;i:1-2;p. 163-172.
Brandt et al., Dipeptidyi-Peptidase IV Converts Intact B-Type Nat . . . , Clinical Chemistry (Baltimore, Md.), 2006, v:52;i:1;p. 82-87.
Dries, Daniel L., Relevance of Molecular Forms of Brain Natriuretic . . . ,Hypertension, 2007, v:49;i:5;p. 971-973.
Heublein et al., Immunoreactivity and Guanosine 3',5'-Cyclic Monoph . . . , Hypertension, 2007, v:49;i:5;p. 1114-1119.
Hunt et al., The Role of the Circulation in Processing pro-Brai . . . , Peptides, 1997,v:18;i: 10;p. 1475-1481.
Gibson et al., The conversion of atrial natriuretic peptide (ANP) . . . , Endocrinology, 1987, v:120;i:2;p. 764-72.
Kawakoshi et al., Identification of a natriuretic peptide (NP) in cy . . . , General and Comparative Endocrinology, 2006, v:148;i:1;p. 41-47.
Kiernan et al., High-Throughput Protein Characterization Using Mas . . . , Analytical Biochemistry, 2002, v:301;i:1;p. 49-56.
Lisy et al., Therapeutic actions of a new synthetic vasoactive . . . , Hypertension, 2001, v:37;i:4;p. 1089-94.
Nelson et al., Mass spectrometric immunoassay, Analytical Chemistry, 1995, v:67;i:7;p. 1153-8.
Niederkofler et al., Novel mass spectrometric immunoassays for the rapi . . . , Journal of Lipid Research, 2003, v:44;i:3;p. 630-9.
Pankow et al., Successive Action of Meprin A and Neprilysin Catab . . . , Circulation Research, 2007, v:101;i:9;p. 875-882.
Shimizu et al., Molecular forms of human brain natriuretic peptide . . . , Clinica Chimica acta, 2002, v:316;i:1-2;p. 129-135.
Singh et al., Novel Snake Venom Ligand Dendroaspis Natriuretic P . . . , Circulation Research, 2006, v:99;i:2;p. 183.
Tsuji et al., Stabilization of human brain natriuretic peptide i . . . , Clinical chemistry (Baltimore, Md.), 1994, v:40;i:4;p. 672-3.
Tsuruda et al., Brain natriuretic peptide is produced in cardiac f . . . , Circulation Research, 2002, v:91;i:12;p. 1127-34.
Tubbs et al., Detection and Quantification of b-2-Microglobulin . . . , Analytical Biochemistry, 2001, v:289;i:1;p. 26-35.
Wu et al., BBA—Serine Protease Cardiac Function, 2005, v:1751;p. 82-94.
Van et al., Carin, A Transmembrane Cardiac Serine Protease, Acts as a Pro-Atrial Natriuretic Peptide-Converting Enzyme; PNAS; vol. 97:8525-8529 (Jul. 18, 2000).
Sawada et al., Co-elevation of brain natriuretic peptide and proprotein-processing endoprotease furin after myocardial Infarction in rats FEBS Letters; 400: 177-182 (1997).
Taylor et al., Curbing activation: Proprotein Convertases in Homeostasis and Pathology, The FASEB Journal; 17:1215-1227 (Jul. 2003).
Sawada et al., Stretch-induced Hypertrophic GroWth of Cardiocytes and Processing of Braintype Natriuretic Peptide Are Controlled by Proprotein-processing Endoprotease Furin, Journal of Biological Chemistry; 272:20545-20554 (Aug. 15, 1997).
Hunt et al, The Role of the Circulation in Processing pro-Brain Natriuretic Peptide (proBNP) to Amino-Terminal BNP and BNP-32; Peptides, 18:1475-1481 (1997).
Benzamidine, Hydrochloride data sheet Calbiochem (accessed at http://www.emdbiosciences.com/oroduct/199001 by Rattan Nath on Dec. 5, 2007).
Wang et al., Nesiritide Does Not Improve Renal Function in Patients With Chronic Heart Failure and Worsening Serum Creatinine, Circulation; 110:1620-1625 (Aug. 30, 2004).
Florowski et al., Low-dose brain natriuretic peptide infusion in normal men and the influence of endopeptidase inhibition, Clin Sci (Lond); 92(3)i: 255-260 (Mar. 1997).
Maisel et al "Rapid Measurement of B-Type Natriuretic Peptide in the Emergency Diagnosis of Heart Failure", N Engl. J. Med. 347:161-167 (Jul. 18, 2002).
Torbjorn Omland, Heart failure in the emergency department—Is B-type natriuretic peptide a better prognostic indicator than clinical assessment?, J. Am. Coll. Cardiol., 44:1334-1336 (2004).
Kawai et al., Plasma Brain Natriuretic Peptide as a Novel Therapeutic Indicator in Idiopathic Dilated Cardiomyopathy During Beta-blocker Therapy: A Potential of Hormone-Guided Treatment, Am. Heart J.; 141:925-932 (2001).
Abassi et al., Implications of the natriuretic peptide system in the pathogenesis of heart failure: diagnostic and therapeutic importance, Pharmacology & Therapeutics; 102:223-241 (2004).
Leuchte et al., Clinical Significance of Brain Natriuretic Peptide in Primary Pulmonary Hypertension, Journal of the American College of Cardiology, 43:764-770 (Mar. 3, 2004).
Berendes et al., Differential Secretion of Atrial and Brain Natriuretic Peptide in Critically III Patient, Anesth. Analg. 93:676-82 (2001).
Jaehde et al., Distribution Kinetics of Enoxacin and Its Metabolite Oxoenoxacin in Excretory Fluids of Healthy Volunteers, Antimicrobial Agents and Chemotherapy; 39: 2092-2097 (Sep. 1995).
Minami et al., Plasma Brain Natriuretic Peptide and N-Terminal Proatrial Natriuretic Peptide Levels in Obese Patients: A Cause or Result of Hypertension? Circulation; 110: e116, (DOI:1 0.1161/01.CI R.000013889344745.F4) (2004).
Benjamin Walcott, The Lacrimal Gland and Its Veil of Tears, News Physiol. Sci.; 13:97-103, (Apr. 1998).
Pereira et al., Long-term stability of endogenous B-type natriuretic peptide during storage at -20 oC for later measurement with Biosite Triage assay, Clinical Biochemistry; 40:1104-1107 (2007).

(56) References Cited

OTHER PUBLICATIONS

Srinivasan et al., Clinical diagnostics on human whole Blood, plasma, serum, urine, saliva, Sweat, and tears on a digital Microfluidic platform, Downloaded on Nov. 28, 2007 by Rattan Nath from http://www.ee.duke.edu/researcn/microfluidics/documents/MicroTAS-Glucose-TD-letter.pdf.

Vanderheyden et al., Brain and other natriuretic peptides: molecular aspects, The European Journal of Heart Failure 6:261-268 (2004).

Prontera et al., Natriuretic Peptides (NPs): Automated Electrochemiluminescent Immunoassay for N-Terminal pro-BNP Compared with IAMAs for ANP and BNP in Heart Failure Patients and Healthy Individuals, Clinical Chemistry; 49:1552-1554 (2003).

AEBSF data sheet from Calbiochem; downloaded on Dec. 5, 2007 by Rattan Nath.

AEBSF data sheet from Roche Applied Science; downloaded on Dec. 5, 2007 by Rattan Nath.

PPACK II data sheet from Calbiochem; downloaded on Dec. 5, 2007 by Rattan Nath.

PPACK data sheet from Calbiochem; downloaded on Dec. 5, 2007 by Rattan Nath.

Cortes et al., Urinary B-Type Natriuretic Peptide Levels in the Diagnosis, and Prognosis of Heart Failure, Journal of Cardiac Failure; 13:549-555 (2007).

Tostsune et al., Urinary immunoreactive brain natriuretic peptide in patients with renal disease, ReQulatorv Peptide; 63:141-148 (1996) (Abstract).

Ng et al., Community Screening for Left Ventricular Systolic Dysfunction Using Plasma and Urinary Natriuretic Peptides, J. Am. Coli. Cardiol.; 45:1043-1050(2005).

Joo et al., Development of an Effective sample Preparation Method for the Proteome Analysis of Body Fluids using 2-D Gel Electrophoresis, Biosci. Biotechnol. Biochem.; 67: 157 4-1577, (2003).

Apple et al., Quality Specifications forB-Type Natriuretic Peptide Assays, Clinical Chemistry 51:1486-1493 (2005).

Schellenberger et al., The precursor to B-type natriuretic peptide is an 0-linked glycoprotein, Archives of Biochemistry and Biophysics; 451: 16G-166 (2006).

\* cited by examiner

METHOD, COMPOSITION AND DEVICE FOR SAMPLING NATRIURETIC PEPTIDES IN A BIOLOGICAL FLUID

CROSS REFERENCE TO RELATED APPLICATIONS

The present application is a continuation of U.S. patent application Ser. No. 15/269,423, filed Dec. 19, 2016, which is a division of U.S. patent application Ser. No. 12/038,355, filed Feb. 27, 2008, the entire contents of both of which are incorporated herein by reference.

BACKGROUND

This disclosure relates generally to sampling natriuretic and other peptides in biological fluids, such as blood, urine and the like. More particularly, it relates to preserving a profile of proteins and peptides of interest in the sampled biological fluid for analysis as continued proteolysis or modification of such peptides and proteins may make subsequent analysis suspect. This disclosure is also useful for monitoring performance of BNP test procedures and biochemical markers used for diagnosis and staging of patients with Congestive Heart Failure ("CHF").

Heart Failure ("HF") compromises ventricular systolic or diastolic function, or both due to cardiac insufficiency. This reflects the inability of the heart to pump sufficient oxygen-rich blood to accommodate the body's needs. CHF further includes the accumulation of fluids in the lungs and breathlessness (dyspnea). The heart responds to this perturbation of fluid homeostasis by secreting natriuretic peptides, which assist in combating the accumulation of fluids in the lungs and other effects of CHF and HF.

Natriuretic peptides are a class of hormones that regulate blood pressure, electrolyte balance, and fluid volume. Natriuretic peptides secondary structure includes a loop formed by an internal disulfide bond between two cysteine residues as shown for Atrial natriuretic peptide ("ANP") and B-type natriuretic peptide (originally referred to as 'Brain Natriuretic Peptide,' ("BNP")) in FIG. 1. Other natriuretic peptides of interest are C-type natriuretic peptide ("CNP") and Dendroaspis natriuretic peptide ("DNP"). The latter was originally isolated from mamba snake venom. See, e.g., US Patent Publication No. 20020082219. CNP is primarily secreted by brain substructures and by the endothelium. It is primarily found in the brain and cerebrospinal fluid with little if any present in the heart.

The structure, function and processing of natriuretic peptides is conserved across species. All known natriuretic peptides seem to have an internal loop formed by a disulfide bond. DNP exhibits further similarity to ANP, BNP and CNP and antibodies to DNP tag some Human epitope(s). DNP has an action similar to that of ANP and BNP, see, e.g., Singh et al. in Circulation Res. (DOI: 10.1161/01.RES0000232322.06633.d3 published online on Jun. 15, 2006), and seemingly has a longer half-life compared to ANP and BNP. See, e.g., Lisy et al. (2001) Hypertension 37, pp. 1089-1094. Indeed, putative homologs of human natriuretic peptides have been isolated in species as distant as fishes including lampreys and hagfishes. See, e.g., Kawakoshi et al. (2006) General and Comparative Endocrinology 148, pp. 41-47. These distantly related peptides exhibit conserved processing and cleavage sites and the loop structure illustrated in FIG. 1.

ANP is a 28-amino acid hormone that originates from the atria of the heart. Within the myocyte, ANP is synthesized as a prepro-ANP (a 151-amino acid peptide), which is cleaved to yield pro-ANP (a 126-amino acid peptide). Pro-ANP is further processed by protease Corin, see, e.g., Wu et al. (2005) Biochimica and Biophysica Acta. 1751:1, pp. 82-94. Pro-ANP can also be processed by protease Furin, at least in vitro, and serum proteases, such as kallikrein and thrombin to yield the 28-amino acid active ANP peptide. See, e.g., Gibson et al. (1987) Endocrinology 120, pp. 764-772. The 28-amino acid ANP peptide is further degraded by a neutral endo-peptidase (EC 3.4.24.11). See, e.g., Wu et al. supra.

BNP is a 32-amino acid peptide secreted by myocytes and fibroblasts in the ventricles in response to increased wall stretch and volume overload. Within the myocyte, BNP is synthesized as prepro BNP (a 134-amino acid peptide), which is cleaved to yield the secreted proBNP (a 108-amino acid peptide). ProBNP is further processed to yield the 32-amino acid active BNP peptide by yet to be definitively identified proteases. In vitro, proteases like Corin, see, e.g., Wu et al. supra, and Furin, see, e.g., Sawada et al. (1997) J. Biol. Chem. 272:33 pp 20545-20554 can process prepro BNP. The 32-amino acid BNP peptide can be further cleaved by endo-peptidases like Dipeptidyl-Peptidase IV to yield a 30-amino-acid active natriuretic peptide, which has been observed in vitro. In vivo, the 30-amino acid peptide is subjected to proteolysis to generate several peptides. Multiple peptide fragments of pro-BNP have been detected in plasma. See, e.g., Shimizu et al. in Clinica Acta. (2002) 316, pp. 129-135. The 32-amino acid BNP peptide may be also generated by proteases in the circulating blood fluids. See, e.g., Hunt et al. (1997) Peptides 18, pp. 1475-1481.

In general, plasma levels of natriuretic peptides reflect a balance between secretion of the propeptide, proteolytic processing and their clearance. BNP is inactivated by proteolysis in addition to receptor-mediated clearance and filtration by kidneys.

Plasma BNP concentration is one of the most sensitive and specific indicator of congestive heart failure. Plasma concentration of BNP related peptides is sharply elevated in patients with CHF. As a result, BNP related peptides are often evaluated in patients arriving at the emergency room with dyspnea. Presently, some assays for the amino portion of pro-BNP detect both pro-BNP and the cleaved N-terminal part of pro-BNP, Nt-proBNP. As a result, the assay fails to accurately estimate pro-BNP levels. Similarly, considerations apply to other assays.

Nt-proBNP and BNP levels are reliable indicators or markers of clinical severity and left ventricular ejection fraction as well as morbidity and mortality. In recent years, Nt-proBNP and BNP have been used to diagnose and classify CHF severity. According to the CHF classification adopted by the New York Heart Association ("NYHA"), the mean concentrations of BNP progressively increase from stage I to IV. For instance, mean BNP concentrations of 71 pg/ml, 204 pg/ml, 349 pg/ml, and 1022 pg/ml corresponded to CHF stages I through IV respectively. Stage IV of CHF represents the highest severity of cardiac disease resulting in inability to carry on any physical activity without discomfort. A patient in this stage of the disease may have symptoms of heart disease or the coronary syndrome even at rest with increasing discomfort if any physical activity is undertaken.

Much of the detectable BNP in circulation in patients suffering from CHF seems to be in the form of relatively inactive precursors or fragments of BNP. Many additional undetectable (by assays in use presently) fragments of BNP may well be circulating with unknown biological effects. See, e.g., Heublein et al. (2007) Hypertension 49, pp.

1114-1119. Sampling errors due to continued processing of BNP related peptide fragments add to the uncertainty in evaluating BNP production by a subject.

Entire BNP, $BNP_{1-32}$, reportedly is a substrate for endopeptidase Dipeptidyl-Peptidase IV (DPP IV), see, e.g., Brandt et al. (2006) Clinical Chemistry 52, pp. 82-87, which shortens it by removing two N-terminal residues to generate $BNP_{3-32}$, which is also biologically active. $BNP_{3-32}$ is further degraded by other proteases, see, e.g., Pankow et al. in Circulation Res. of Sep. 6, 2007 online publication D01: 10.1161/CIRCRESAHA.107.153585 to generate additional peptides. Proteases like thrombin, plasmin and the like are also capable of cleaving pro-BNP at least in vitro. See, e.g., Hunt et al. supra. Such proteolysis is expected to add to sampling errors due to continued proteolysis of sampled BNP. BNP also induces Matrix Metalloproteinases. See, e.g., Tsuruda et al. (2002) Circulation Res. 91, pp. 1127. Some metalloproteinases are known to further proteolyze BNP, see, e.g., Pankow supra. Thus, a large number of proteases are a potential source of sampling errors.

As a result, sampling the blood or another biological fluid from a patient typically provides an inaccurate representation of BNP related peptides, information that is important for diagnostic applications and other uses. See, e.g., Daniel L. Dries (2007) Hypertension 49, pp. 971-973. This lack of clarity is due to the possibility that BNP related peptides continue to be subject to proteolysis after sampling, including proteolysis by proteinases induced by BNP or the act of sampling itself.

There have been many attempts to employ sampling and processing methods to reduce or eliminate the artifacts introduced by such ongoing proteolysis. Many serine proteases are known to act on BNP, its proteolytic products or its precursors. For non-fluid tissues, boiling in water is assumed to inactivate proteases. See, e.g., Hunt et al. in Peptides (1997) 18, pp. 1475-1481. Investigators purifying BNP from tissue have reported the use of serine proteases inhibitors like aprotinin or a combination of aprotinin and benzamidine for preventing BNP proteolysis. See, e.g., Tsuji et al. in Clin. Chem. (1994) 40, pp. 672-3. Among the many suggestions for controlling induction of proteases by the act of sampling is the use of plastic tubes. Also available are blood collection tubes containing protease inhibitors. An example is BD P100 v1.1 blood collection vacuum tubes (Becton, Dickinson, and Company catalog no. 8013142). Protease inhibitors like PPACK I, PPACK II and Protease inhibitor cocktail set III from Calbiochem provide broad spectrum protease inhibition. However, these inhibitors are not entirely suitable for applications such as sampling natriuretic peptides and their fragments or precursors due to both technical limitations and their cost (see infra). When sampling blood, protease inhibitors like AEBSF and Benzamidine have been used to arrest proteolysis at relatively low concentrations—in part to avoid covalent modification of the sampled proteins.

Many insufficiently effective approaches have been adopted to reduce proteolysis of BNP and other peptides. These methods include use of plastic tubes or adding EDTA to the collected samples or broad-spectrum protease inhibitors ROCHE™ supplies AEBSF (4-(2-Aminoethyl) benzenesulfonyl fluoride hydrochloride), a water-soluble serine protease inhibitor with a molecular weight of 239.5 Da under the trade name PEFABLOC SC™. AEBSF inhibits proteases like chymotrypsin, kallikrein, plasmin, thrombin, and trypsin. Typical working concentrations are in the range of at 0.1-1.0 mM with stock solutions at 100 mM.

As to AEBSF, ROCHE™ provides notice that at high concentrations it forms covalent adducts with proteins and peptides. Thus, such inhibitors are used at about the recommended concentration range, see, e.g., the disclosed use of AEBSF at 0.125 mM in US Patent Publication No. 2006/0183681 (discussed infra). However, ROCHE™ also sells a proprietary composition together with the inhibitor in a package, e.g., PEFABLOC SCPLUS™ (or PEFABLOC SC PLUS™). It is unknown if formation of adducts is adequately prevented at concentrations of interest for sampling blood and plasma like fluids. Further, as discussed above, proteases in addition to serine proteases are responsible for and capable of degrading BNP and related peptides in plasma, which proteases are not effectively inhibited by AEBSF.

An illustrative example, US Patent Publication No. 2006/0183681 ("the '681 publication") describes well-known protease inhibitors to prevent further hydrolysis of BNP. The '681 publication teaches preparing a serum based standard, see, e.g., paragraph 42 of the '681 publication, by pooling sampled blood plasma, defibrinating it followed by delipidizing it and then adjusting the total protein concentration followed by the addition of protease inhibitors benzamidine and AEBSF to a final concentration of 9.5 mM and 0.125 mM respectively and then spiking it with a predetermined amount of BNP. This serum-based preparation is stable for several days at –20° C. The publication does not describe the process by which plasma is obtained or the effect of the long time taken to process the sampled plasma on the level of endogenous BNP and peptides related to it. Indeed, sampling biological fluids is not addressed nor are problems peculiar to such sampling identified or any solutions suggested.

US Patent Publication 2004/0067889 ("the '889 Publication") discloses compositions for preserving BNP in sampled biological fluids. The '889 Publication discloses that protease inhibitors PPACK and PPRACK are most effective in arresting proteolysis of BNP in sampled blood or plasma. Further, these inhibitors are effective alone or in combination with AEBSF, leupeptin and antipain as well as benzamidine. The '889 Publication posits that structural similarity between protease inhibitors and regions of BNP is responsible for the effectiveness of the protease inhibitors in stabilizing BNP.

The '889 Publication does not disclose effective and efficient compositions for sampling a biological fluid and preserving a peptide profile therein based on synergy between two or more constituents of the compositions. Further, the '889 Publication does not disclose efficient and effective protease inhibitor compositions that do not exhibit artifacts due to formation of adducts with the sampled peptide or protein. Indeed, PPACK and PPACK II are expensive protease inhibitors, indeed significantly more expensive than AEBSF. Therefore, an efficient method for preventing proteolysis after sampling is not disclosed to one having ordinary skill in the art.

A number of point-of-care diagnostic tests for BNP are available. ABBOTT AxSYM™, BAYER ADVIA CENTAUR™, and BIOSITE TRIAGE™ BNP assays are some of the most widely used quantitative test methods for determination of BNP. The ABBOTT AxSYM™ assay utilizes the Microparticle Enzyme Immunoassay (MEIA) technology, which uses microparticles coated with anti-BNP monoclonal antibodies that bind to human BNP antigen. These antigen-antibody complexes on the microparticles bind a monoclonal anti-BNP alkaline phosphatase conjugate capable of yielding a fluorescent product. The fluorescent intensity is used to determine BNP levels. The BIOSITE TRIAGE™

BNP assay is an immunofluorometric assay. In this assay, a rabbit recombinant polyclonal antibody is bound to the fluorescent label, and a murine monoclonal antibody against the disulfide bond-mediated ring structure of BNP is bound to the solid phase. In this assay plasma is treated with fluorescent antibody conjugates and complexes of BNP and the fluorescent antibody conjugate are captured on a detection lane. The concentration of BNP in the specimen is proportional to the fluorescence from bound complexes. The BAYER ADVIA CENTAUR™ assay is a two-site sandwich immunoassay with an acridinium ester labeled monoclonal mouse anti-human BNP (specific to the ring structure on BNP) as the first antibody and a biotinylated monoclonal mouse anti-human antibody (specific to the C-terminal portion of BNP) as the second antibody (solid phase). The complex is further coupled to streptavidin magnetic particles. The lower limits of detection for the ABBOTT AxSYM™, BIOSITE TRIAGE™, and BAYER ADVIA CENTAUR™ BNP assays are 15, 5, and 2 pg/mL, respectively.

BNP and similar peptides exhibit poor stability in serum or plasma. BNP is cleared from circulation by specific cellular receptors and proteases including endopeptidases. A reason for the poor stability of BNP, in addition to proteolysis by multiple natural proteases in plasma or serum, is due to excretion by the kidneys and clearance by uptake through Natriuretic Peptide Receptor C (NPR-C), which in kidneys is primarily distributed in the podocyte region. NPR-C potentially provides a mechanism to down regulate BNP levels. As a result, the half-life ($t_{1/2}$) of BNP in vivo is of the order of approximately 20 minutes or so.

Notwithstanding the above difficulties, plasma BNP concentration is a preferred marker for diagnosis and prognosis of cardiac function and acute myocardial infarction. Plasma concentrations of BNP increase with a decline in heart function. Potentially BNP can serve as the preferred biochemical marker for pre-screening patients for further cardiac investigations and/or treatment. However, the limited stability of sampled BNP makes this difficult. In vitro, BNP is rapidly proteolyzed, for example, within 24 h of separation of plasma from whole blood. See, e.g., Belenky et al. in Clinica Chimica Acta (2004) 340, 163-172. Progressive degradation during refrigerated storage makes accurate measurement of BNP challenging.

Thus, currently used quantitative tests for BNP likely include avoidable errors due to continued proteolysis of proBNP and BNP fragments after sampling. Such errors may result in either overestimation or underestimation of circulating BNP related peptide species.

The sampling technique itself becomes important for determining the level of the peptide of interest in general even in case of peptides other than natriuretic peptides.

Therefore, there exists a need for a sampling method, device and composition to allow accurate sampling of BNP and other peptides in biological fluids for subsequent assays.

SUMMARY

Disclosed herein are both the problems underlying sampling biological fluids for analysis of peptides therein and solutions thereto. More specifically, disclosed is a composition that synergistically prevents proteolysis of peptides in sampled biological fluids using sulfonyl fluoride family protease inhibitors at high concentrations combined with at least one additional protease inhibitor of a different type, preferably a broad spectrum protease inhibitor, and a chelator. A preferred embodiment uses AEBSF at 10 mM, Benzamidine at 20 mM and ethylenediamine tetracetic acid ("EDTA"). In another preferred embodiment, Benzamidine can be replaced by leupeptin, an inhibitor of lysosomal proteases. The disclosed composition may be combined with other protease inhibitors to further modulate its specificity, for instance to additionally target acid proteases.

Disclosed preferred compositions combine a sulfonyl fluoride protease inhibitor with another protease inhibitor in a proportion to essentially eliminate the formation of adducts due to the sulfonyl fluoride protease inhibitor being at a final concentration above or about 2.5 mM, and a chelator. The sulfonyl fluoride protease inhibitor is used at various high concentrations, such as 10 mM in another preferred embodiment. Additional protease inhibitors, reducing agents, stabilizers and buffering agents may be combined with the preferred compositions.

The disclosed compositions synergistically not only prevent proteolysis by proteases present in sampled biological fluids, but also arrest the formation of adducts on proteins and peptides of interest, a common problem in using sulfonyl fluoride based protease inhibitors while broadening the extent of inhibition of proteolysis and preventing the coagulation of blood. Samples collected using the disclosed compositions, for instance in devices incorporating the same, may be stored at room temperature for several hours or frozen for later analysis after even several months. Most specifically, this composition is useful for sampling and determining the level of natriuretic peptides like BNP.

The peptides of interest include natriuretic peptides (native, synthetic, or recombinant). The peptide profile may include contributions from a synthetic natriuretic peptide, including when the level of an administered or induced natriuretic peptide is monitored. Preferably, the sampled peptide or protein profile is that of a naturally occurring natriuretic peptide. Preferably, the administered or induced natriuretic peptide is selected from the set consisting of ANP and BNP. More specifically, the disclosure includes sampling mammalian, including human, plasma or serum, especially human plasma or serum, and more particularly, processed human plasma. Still more specifically is disclosed the effectiveness of one or more optionally substituted alkyl or aryl sulfonyl fluoride protease inhibitors and benzamidine or another broad spectrum protease inhibitor or a lysosomal protease inhibitor in preserving the peptide profile for subsequent analysis.

Therefore, disclosed herein is a composition of matter for sampling a protein profile in a biological fluid of interest, comprising an effective amount of a first alkyl or aryl sulfonyl fluoride protease inhibitor and an effective amount of a second protease inhibitor selected from the group consisting of a lysosomal protease inhibitor and an additional broad spectrum protease inhibitor, wherein the additional broad spectrum protease inhibitor inhibits serine proteases; and an effective amount of chelator. This combination also prevents coagulation of blood if blood is the sampled biological fluid.

Notably, essentially no adducts are formed in the sampled protein profile due to the presence of the sulfonyl fluoride protease inhibitor. This combination of chelator and protease inhibitors is economical, easy to manufacture and leaves the sampled biological fluid essentially unmodified by the formation of adducts even when the samples are stored for two hours at room temperature and/or for six months at seventy degrees centigrade below zero.

In a preferred embodiment, the disclosed composition contains as the chelator, ethylene diamine tetracetic acid. In a preferred embodiment, the disclosed composition includes as the first protease inhibitor AEBSF. In a preferred embodiment, the disclosed composition includes as the second protease inhibitor benzamidine. Alternatively, the second protease inhibitor may be selected to be leupeptin.

An alternative to the choice of AEBSF as the first protease inhibitor is a sulfonyl fluoride is selected from (2-aminoethyl)-benzenesulfonyl fluoride, phenylmethanesulfonyl fluoride, 4-amidinophenyl-methanesulfonyl fluoride, 3-acetyl benzenesulfonyl fluoride, 2-aminobenzenesulfonyl fluoride, 3-(3-chlorophenoxyacetamido)benzenesulfonyl fluoride, and peptide aminobenzene sulfonyl fluorides.

Also disclosed are devices useful for sampling a protein profile in a biological fluid of interest, comprising a component for receiving a fluid fraction of the biological fluid, the component containing an effective amount of a first alkyl or aryl sulfonyl fluoride serine protease inhibitor; and an effective amount of a second protease inhibitor selected from the group consisting of a lysosomal protease inhibitor and an additional broad spectrum serine protease inhibitor; and wherein the sampled protein profile is not modified by the formation of adducts due to the protease inhibitors upon incubation for at least four hours at room temperature. The protease inhibitor-chelator composition may be present in a solid form, including a lyophilized form, or as a liquid. This combination is economical, easy to manufacture and leaves the sampled biological fluid essentially unmodified by the formation of adducts even when the samples are stored for four hours at room temperature and/or for six months at seventy degrees centigrade below zero.

Also disclosed is a method for sampling a biological fluid by adding an effective amount of metal chelator upon sampling the biological fluid, adding an effective amount of a first alkyl or aryl sulfonyl fluoride serine protease inhibitor, and adding an effective amount of a second protease inhibitor selected from the group consisting of a lysosomal protease inhibitor and an additional broad spectrum serine protease inhibitor. This combination is economical, easy to manufacture and leaves the sampled biological fluid essentially unmodified by the formation of adducts even when the samples are stored for four hours at room temperature and/or for six months at seventy degrees centigrade below zero.

These and other features are described with the assistance of the illustrative figures and charts described next.

DETAILED DESCRIPTION

Figure 1:
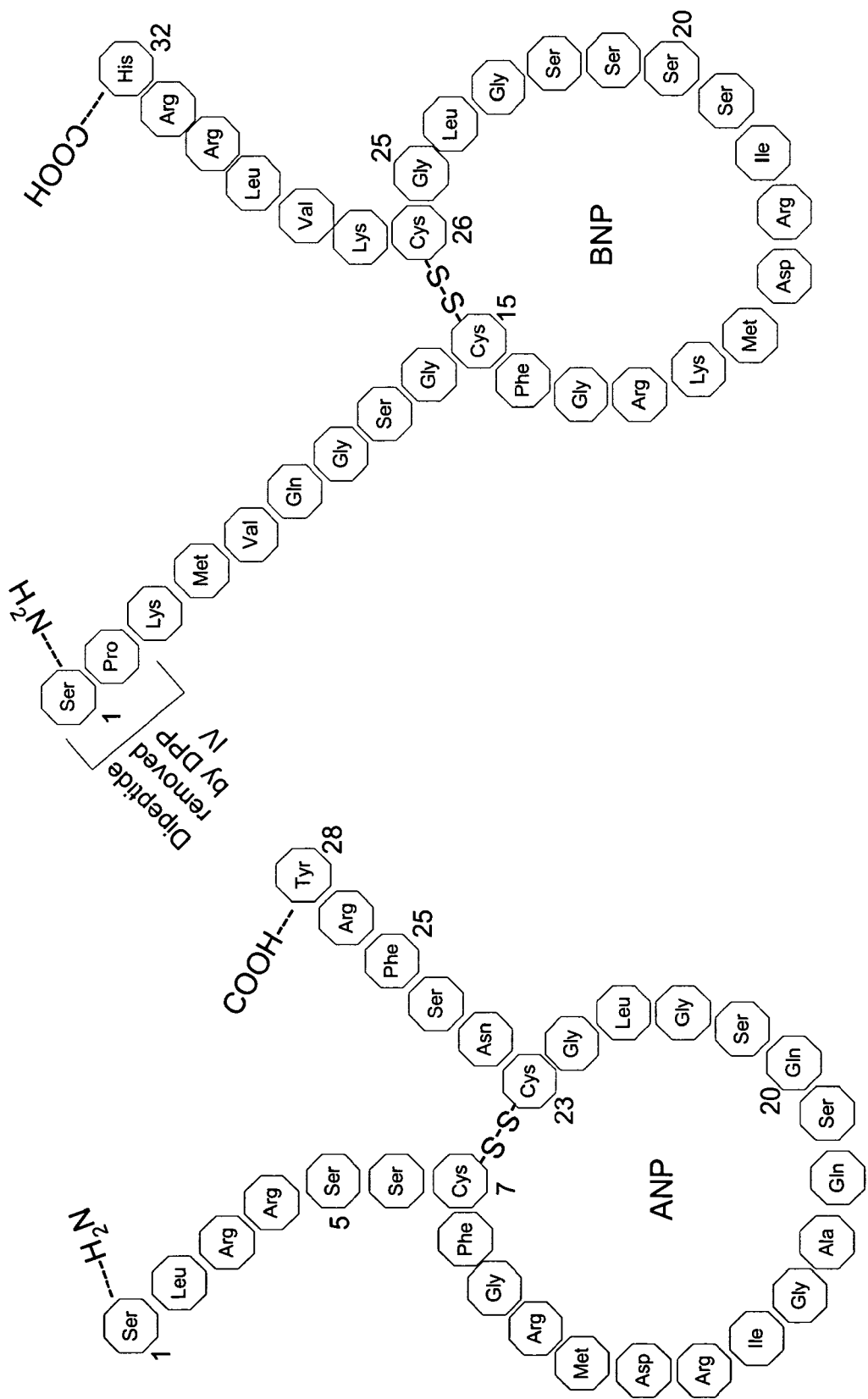
FIG. 1 shows the amino acid sequence and the two dimensional structure of ANP and BNP.

The disclosure enables sampling of biological fluids to preserve the profile of peptides therein, for instance to monitor the level or effectiveness of natriuretic peptides, such as ANP, BNP, CNP and DNP. The samples are also useful for assaying for peptides other than natriuretic peptides.

As used herein, the terms "natriuretic peptide" and "natriuretic peptides" include such peptides in general, particularly ANP, BNP, CNP and DNP, as well as precursors of such peptides such as pro- and prepro-peptides, for example proBNP and preproBNP described above. This term includes such substances whether exogenous or endogenous, whether existing naturally, or synthesized, or prepared using recombinant DNA techniques.

As used herein, "effective amount" is the amount of a substance that can be determined without undue experimentation in view of this disclosure and the current state of the art. An effective amount of a protease inhibitor or chelator is the weight or volume added to an expected volume of sampled biological fluid to ensure the concentration of the protease inhibitor or chelator is at or above the effective concentration. Such a volume of sampled biological fluid may be referred to as an effective volume.

Sulfonyl fluorides exhibiting serine protease inhibitory activity in combination with one or more of lysosomal protease inhibitors leupeptin, and broad spectrum protease inhibitors like benzamidine are suitable for use in the disclosed compositions. Notably, preferred protease inhibitors inhibit serine protease activity and can react covalently with the serine residue at the catalytic site of serine proteases.

The sulfonyl fluorides suitable for use in the compositions, kits and methods of this disclosure include optionally substituted alkyl and aryl sulfonyl fluorides and inhibit proteolytic activities of trypsin, chymotrypsin, elastase, plasmin, thrombin, or kallikrein (using substrates such as labeled casein or other suitable peptide substrates).

The term "alkyl" as used herein means a straight or branched chain, or non-aromatic cyclical, hydrocarbon radical, or combination thereof including optionally substituted variations. Permissible substituents include those commonly found for such moieties, provided that they do not significantly interfere with the protease-inhibiting activity of the compound in question.

As used herein, "aryl" refers to a polyunsaturated, typically aromatic, hydrocarbon substituent, including optionally substituted variations.

This disclosure bases the suitability of alkyl and aryl sulfonyl fluorides as components in a sampling device, composition or method, in part, on the ability of the disclosed combinations to overcome adduct formation while providing broad spectrum protease inhibition for sample preservation in view of the proteases encountered in sampled biological fluids, such as human serum or plasma, that rapidly cleave natriuretic peptides, as described in this disclosure.

A preferred protease inhibitor in the sulfonyl fluoride class is (2-aminoethyl)-benzenesulfonyl fluoride (AEBSF, Formula: $C_8H_{10}NO_2SF.HCl$, Molecular Weight: 239.7). It shows broad inhibitory activity with slow hydrolysis under weak basic conditions (pH 8-9) and is water-soluble. Other candidate sulfonyl fluorides include, for example, methanesulfonyl fluoride, phenylmethanesulfonyl fluoride (PMSF).

A useful addition in a preferred embodiment, to sulfonyl fluoride protease inhibitors is Benzamidine (Formula: $C_6H_5C(NH)NH_2HCl$, Molecular Weight: 156.6), which is a broad-spectrum protease inhibitor that also inhibits serine proteases.

A useful addition in a preferred embodiment, to sulfonyl fluoride protease inhibitors is Leupeptin, which is a broad-spectrum lysosomal protease inhibitor that also inhibits serine proteases.

A useful addition to sulfonyl fluoride protease inhibitor containing combinations of two or more protease inhibitors is a chelator. In a preferred embodiment, the chelator is ethylenediamine tetracetic acid ("EDTA").

Additional useful additions to the disclosed compositions of two or more protease inhibitors, at least one of which is a sulfonyl fluoride, and a chelator are additional protease inhibitors and their mixtures.

In general, to provide satisfactory stability for the natriuretic peptide, the sulfonyl fluoride and benzamidine protease inhibitor is employed in an appropriate amount. Thus, sampling devices, compositions and methods use about 5.0 mM to about 100 mM, preferably from about 10 mM to about 50 mM of the sulfonyl fluoride protease inhibitor in combination with about 5.0 mM to about 100 mM, preferably from about 10 mM to about 50 mM, and most preferably about 20 mM of benzamidine protease inhibitor. In alternative embodiments, a broad-spectrum lysosomal protease inhibitor like leupeptin may be used instead of or in addition to benzamidine. The concentration of leupeptin is preferably about 2.5 mM or more, more preferably about 5.0 mM or more, and most preferably about at least 10 mM. Such concentrations of protease inhibitors are referred to herein as "an effective amount" because they substantially prevent the formation of adducts due to the use of sulfonyl fluorides while enhancing broad-spectrum protease inhibition, particularly in combination with a chelating agent like EDTA.

The following examples and description illustrate the compositions and embodiments incorporating the compositions disclosed herein.

The desirability of measuring the levels of various species of natriuretic peptides has been discussed (supra) in the context of BNP and diagnosis/prognosis of heart failure (HF) and disturbances in fluid homeostasis. It is further desirable to preserve the sampled peptide profile without chemical modifications due to the formation of adducts or continued proteolysis.

Natriuretic peptides are not only important markers of heart failure and other disordered involving fluid homeostasis; they are also of significance in therapeutic settings. Many clinical trials and patient investigations, result in the need to preserve biological fluid samples for later analysis or for comparison with samples of other patients and standards. This requires careful preservation of the peptide profile present at the time samples are collected. The disclosed composition provides a solution to this problem.

Simple pro-BNP processing scheme suggests 2 circulating pro-BNP derived peptides, which are assumed to be detected by commercially available BNP or NT-pro-BNP assays. However, there is evidence that additional forms of BNP are present in circulation and other biological fluids because BNP-32 undergoes further hydrolysis, generating a BNP form that lacks the two N-terminal amino acid residues ($BNP_{3-32}$ or $proBNP_{79-108}$) due to the action of DPP IV. The extent of proteolysis encountered makes interpretation and evaluation of data difficult, especially after passage of time. Further, robust point-of-care devices that do not require immediate access to refrigeration is complicated by the proteolysis. This proteolysis is further described in Example 1 and Table 1.

Example 1

In order to observe, characterize and identify the BNP hydrolysis products a Mass Spectrometric Immunoassay (MSIA) was developed and employed in the analysis of BNP. This technique is broadly described in, e.g., Nelson et al. (1995) Anal. Chem. 67, 1153-1158; Tubbs et al. (2001) Anal. Biochem. 289, 26-35; Kiernan et al. (2002) Anal. Biochem. 301, 49-56; Niederkofler et al. (2003) J. Lipid Res. 44, 630-639 and U.S. Pat. Nos. 6,783,672; 6,974,704; 7,083,723; 7,083,724; 7,087,163; 7,087,164; 7,087,165; and 7,087,163. The basic methodology is described in the context of BNP although the technique is also applicable to ANP and other peptides of interest.

Figure 2:
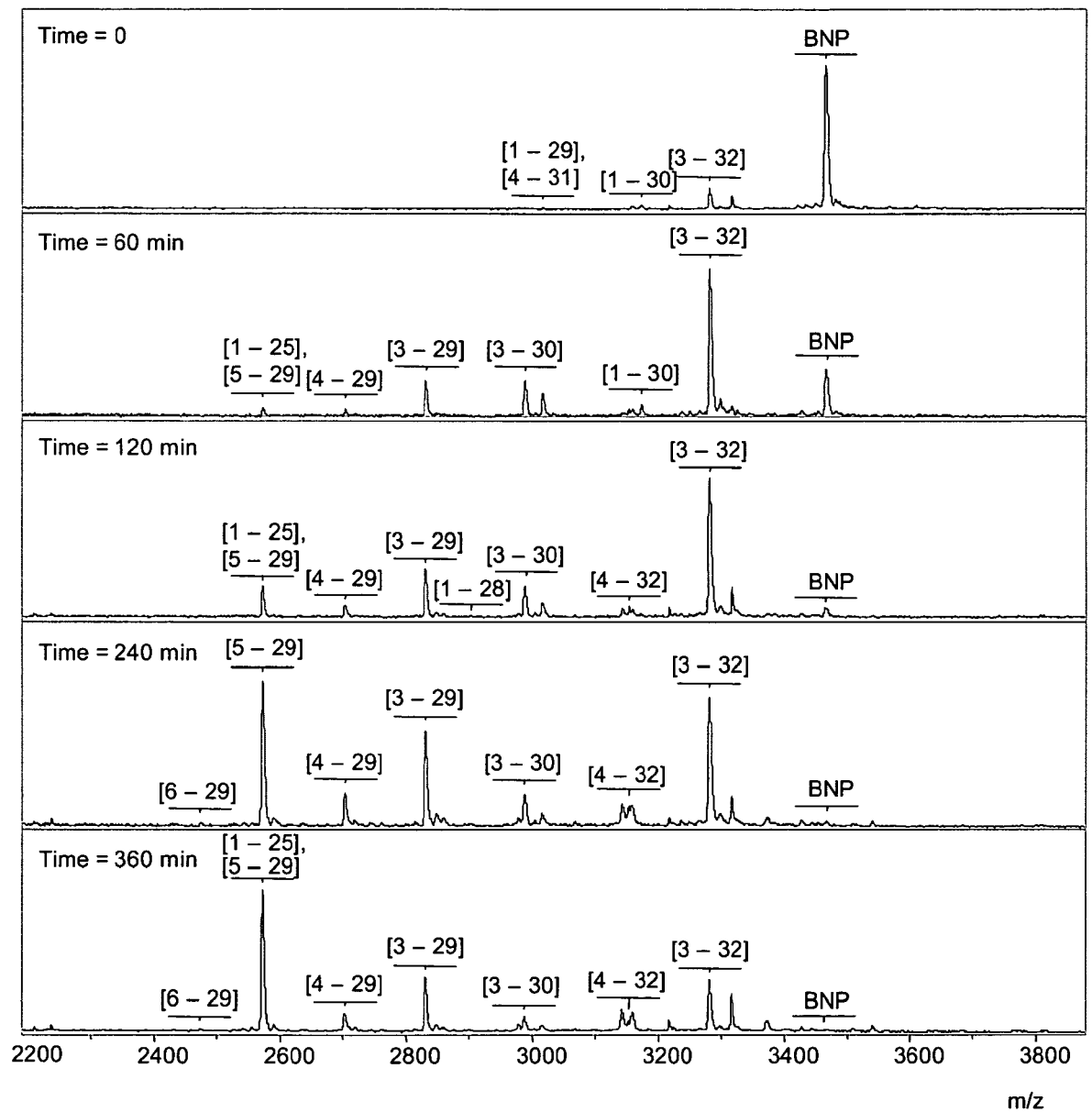
FIG. 2 depicts the time course of $BNP_{1-32}$ proteolysis as revealed by mass spectrometry ("MSIA"). $BNP_{1-32}$ was added to heparin plasma at 100 ng/mL and followed by incubation at room temperature for 6 hours. Aliquots were removed and analyzed by MSIA every hour to monitor the progress of BNP proteolysis.

Briefly, MSIA entails the use of affinity capture, to extract BNP and many of its' hydrolysis products for mass spectrometric detection, to observe and identify products of BNP hydrolysis. Therefore, synthesized $BNP_{1-32}$ was added to room temperature plasma (from blood collected in heparinized blood collection tubes). At a several times post-spiking $BNP_{1-32}$ into the plasma, aliquots of the spiked plasma were analyzed to monitor the progress of BNP.sub.1-32 hydrolysis. The results of performing a series of analyses on aliquots removed and analyzed every hour for up to six hours post-addition of $BNP_{1-32}$ at 100 ng/mL are shown in FIG. 2. The analysis at time zero shows a large dominant peak corresponding to $BNP_{1-32}$, as indicated by the appearance of a peak at 3465.8 m/z (in agreement with the theoretical mass of $BNP_{1-32}$, 3465.08), as well as products of BNP hydrolysis indicated by the presence of peaks at 3280 m/z, 3171 m/z and 3015 m/z corresponding to the masses of $BNP_{3-32}$, $BNP_{1-30}$ and $BNP_{1-29}$ or $BNP_{4-31}$. The last two species are indistinguishable in the chart due to similar amino acid compositions. The molecular weight for each of the identified BNP hydrolysis peptides is given in TABLE 1 below:

TABLE 1

MOLECULAR WEIGHTS OF VARIOUS BNP FRAGMENT

| BNP [aa] | [1-32] | [3-32] | [2-31] | [1-30] |
|---|---|---|---|---|
| MW | 3465.08 Da | 3280.88 Da | 3240.86 Da | 3171.75 Da |
| BNP [aa] | [4-32] | [1-29] or [4-31] | [3-30] | [1-28] | [4-30] |
| MW | 3152.71 Da | 2987.56 Da | 2902.40 Da | 2859.38 Da | 3015.56 Da |
| BNP [aa] | [2-28] | [4-29] | [4-28] | [1-25] or [5-29] | [6-29] |
| MW | 2815.33 Da | 2703.19 Da | 2590.04 Da | 2473.87 Da | 2572.00 Da |

As $BNP_{1-32}$ incubates in the plasma at room temperature, it continues to hydrolyze, creating even more of the previously observed hydrolysis products as well as even smaller ones. Four hours after the addition of $BNP_{1-32}$ to room temperature plasma, all of the $BNP_{1-32}$ appears to have been processed into smaller peptides, with the dominant species $BNP_{3-32}$, $BNP_{1-25}$ and $BNP_{529}$ (with the last two being indistinguishable from one anther due to their similar amino acid composition).

Figure 3:
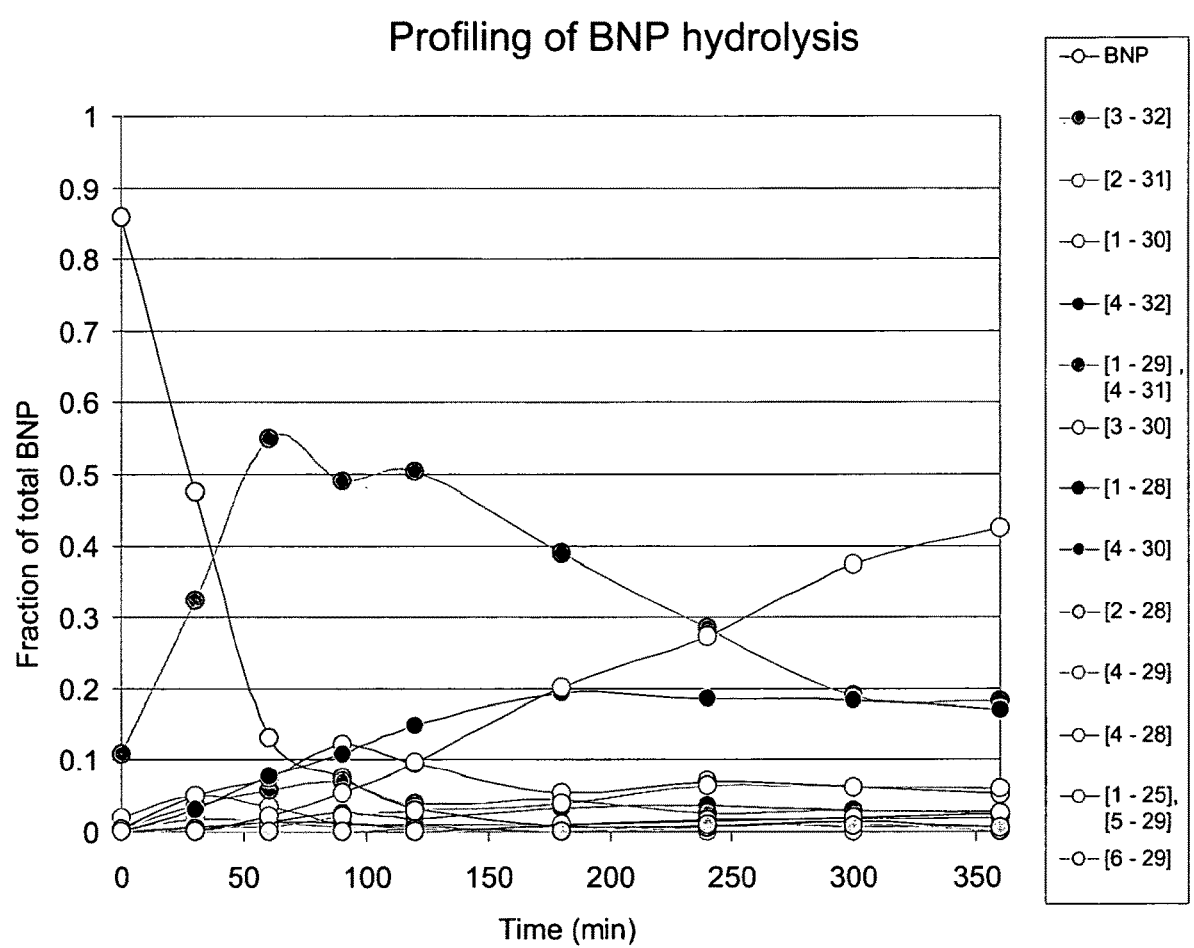
FIG. 3 shows the time course of BNP species as a fraction of total BNP species during BNP proteolysis. Each of BNP species is estimated from the intensity of its peak in the mass spectra of FIG. 2.

Plotting the percentage of each species with respect to the total amount over time, the rate at which one peptide is produced and then processed into smaller peptides can be illustrated as is shown in FIG. 3. This type of plot is useful for monitoring BNP hydrolysis and the efficiency of protease inhibitors in preventing the $BNP_{1-32}$ hydrolysis.

Example 2

Studies to identify protease inhibitors able to prevent $BNP_{1-32}$ hydrolysis began with screening. First tested was the protease inhibitor cocktails used in the Becton Dickinson collection tubes (BD P100 v.1.1 tubes).

Figure 4:
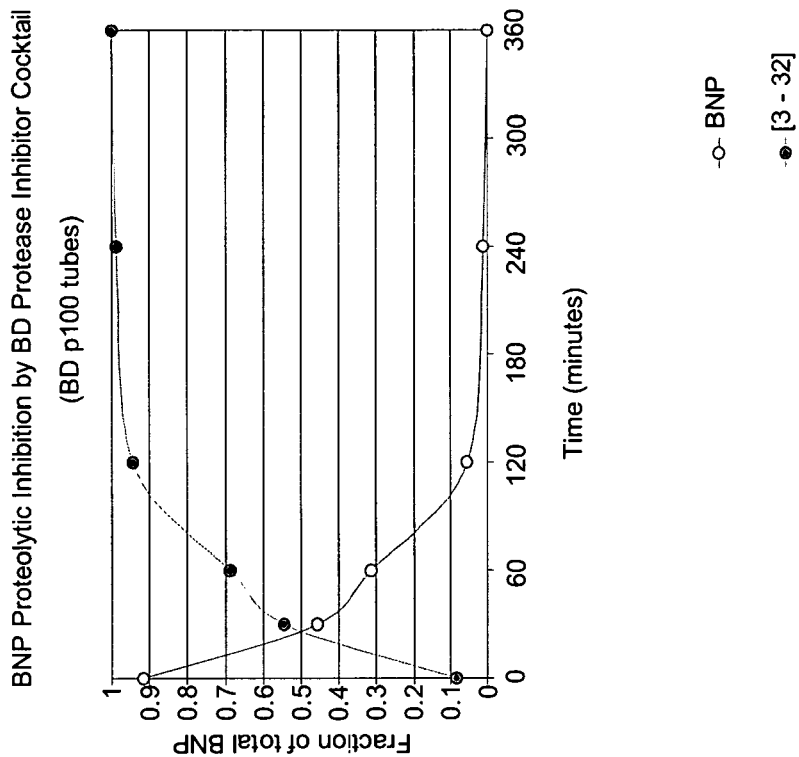
FIG. 4 shows BNP proteolysis in blood collected using BD P100 blood collection tubes. The time course shows that the protease inhibitors in BD P100 prevent the hydrolysis from proceeding beyond the formation of $BNP_{1-32}$.
Figure 4:
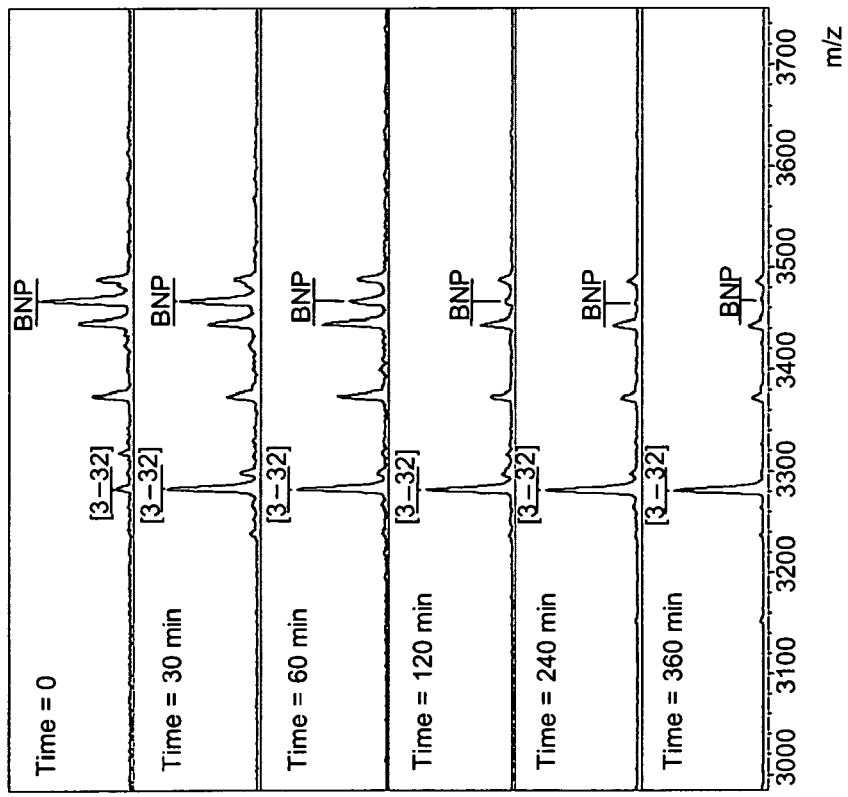

Commercially available protease inhibitor cocktail in the BD P100 v1.1 blood collection vacuum tubes (Becton, Dickinson, and Company catalog no. 8013142) was tested for arresting the hydrolysis of BNP. Shown in FIG. 4 are the illustrative results of sequentially analyzing samples from plasma that was provided from blood collected using BD P100 v1.1 and spiked with $BNP_{1-32}$. Observed in each of the mass spectra are two species of BNP, the intact form of $BNP_{1-32}$ and the truncated BNP form of $BNP_{3-32}$ due to hydrolysis of $BNP_{1-32}$. The plot of percentage of BNP species over time shows that after only 30 minutes half of the $BNP_{1-32}$ has been converted into $BNP_{3-32}$, demonstrating the inability of the protease inhibitors provided by the BD P100 to prevent the hydrolysis of $BNP_{1-32}$.

Example 3

Figure 5:
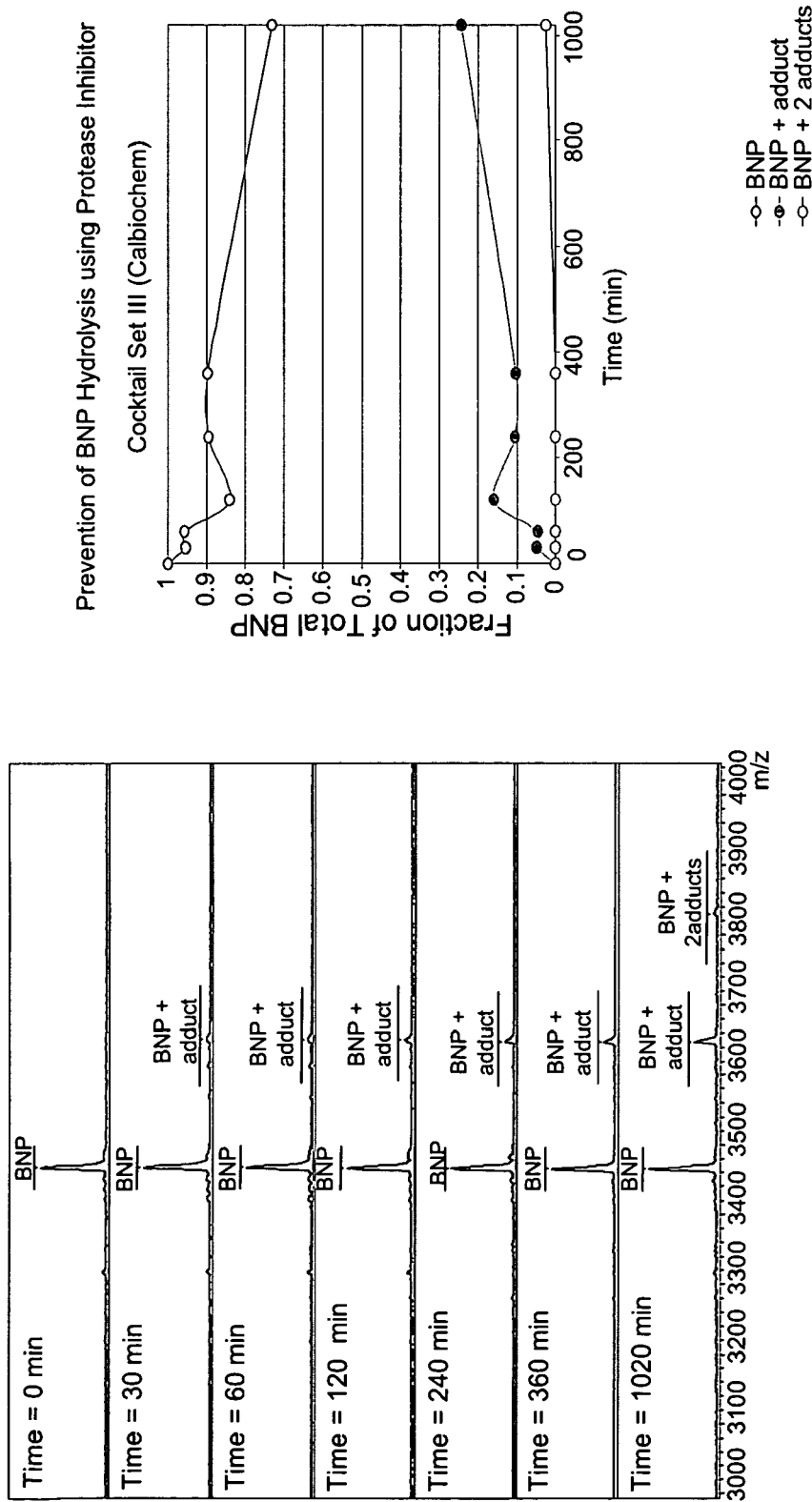
FIG. 5 shows BNP proteolysis in plasma treated with the protease inhibitor cocktail set III (EMD catalog no. 535140). The time course shows that the protease inhibitors reduce BNP hydrolysis, and also lead to the generation of covalent adducts over time (indicated by the peaks at higher m/z).

Another commercially available cocktail of protease inhibitors tested was the protease inhibitor cocktail set III (diluted 1 to 10 in plasma) provided by EMD (catalog no. 535140). Once again, heparin plasma was treated with this protease inhibitor cocktail set followed by the addition of $BNP_{1-32}$ and incubation at room temperature. Aliquots were collected—+every 30 to 60 minutes and tested for BNP hydrolysis. The results of the mass spectral analyses of the aliquots, as well as the plot of the percentage of BNP species over time are shown in FIG. 5. Observed is that protease inhibitor cocktail set III prevents or slows the hydrolysis of $BNP_{1-32}$, but in addition to preventing the hydrolysis of BNP, the protease inhibitor cocktail results in adduct formation, which adducts are indicated by the peaks located at a slightly higher mass than the $BNP_{1-32}$. The extent of adduct formation increases significantly with incubation time.

Protease inhibitor cocktail set III consists of 100 mM AEBSF hydrochloride (Calbiochem catalog no. 101500), 80 µM Aprotinin (Calbiochem catalog no. 616371), 5 mM Bestatin (Calbiochem catalog no. 200484), 1.5 mM E-64 (Calbiochem catalog no. 324890), 2 mM Leupeptin hemisulfate (Calbiochem catalog no. 108975), a lysosomal protease inhibitor, and 1 mM Pepstatin A (Calbiochem catalog no. 516482), which is an acid protease inhibitor.

Nevertheless, cocktail set III is not satisfactory because it is unable to faithfully preserve the profile of the peptides and fragments of interest, which in this case is BNP.

Example 4

Next, the individual protease inhibitors, including some of those included in protease inhibitor cocktail set III (EMD) were tested using the protocols described supra.

Briefly, aliquots of heparin plasma were treated with each one of the protease inhibitors. To each aliquot of plasma, $BNP_{1-32}$ was added at 10 ng/mL and incubated at room temperature. Aliquots were sequentially removed and analyzed for BNP hydrolysis.

Figure 6:
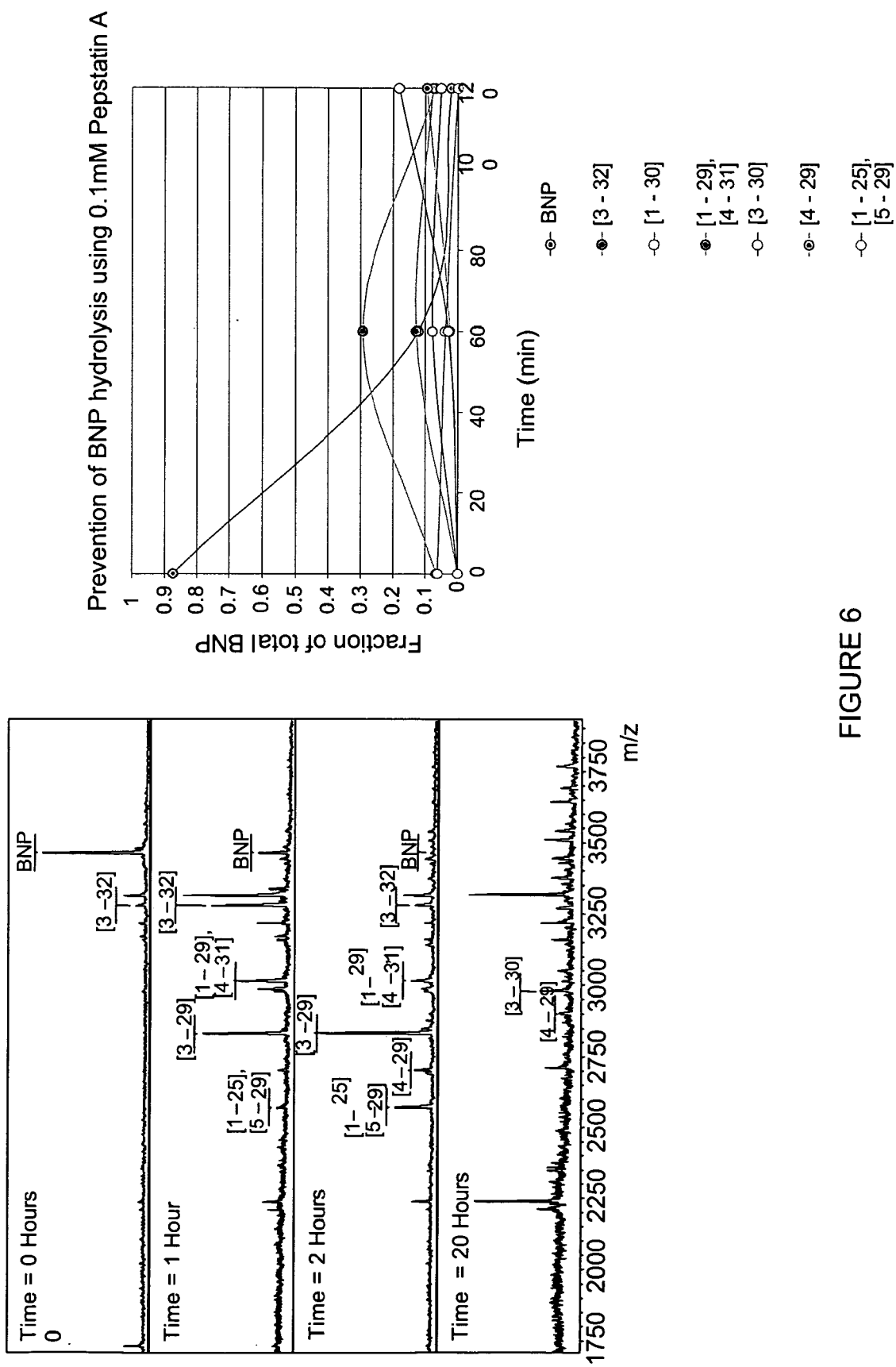
FIG. 6 shows BNP proteolysis in plasma treated with the protease inhibitor Pepstatin A (Calbiochem catalog no. 516482). The time course of both the mass spectra and the composition of BNP show little or no effect on BNP proteolysis.

Pepstatin A at 0.1 mM did not appreciably prevent the hydrolysis of BNP, as illustrated in FIG. 6.

Figure 7:
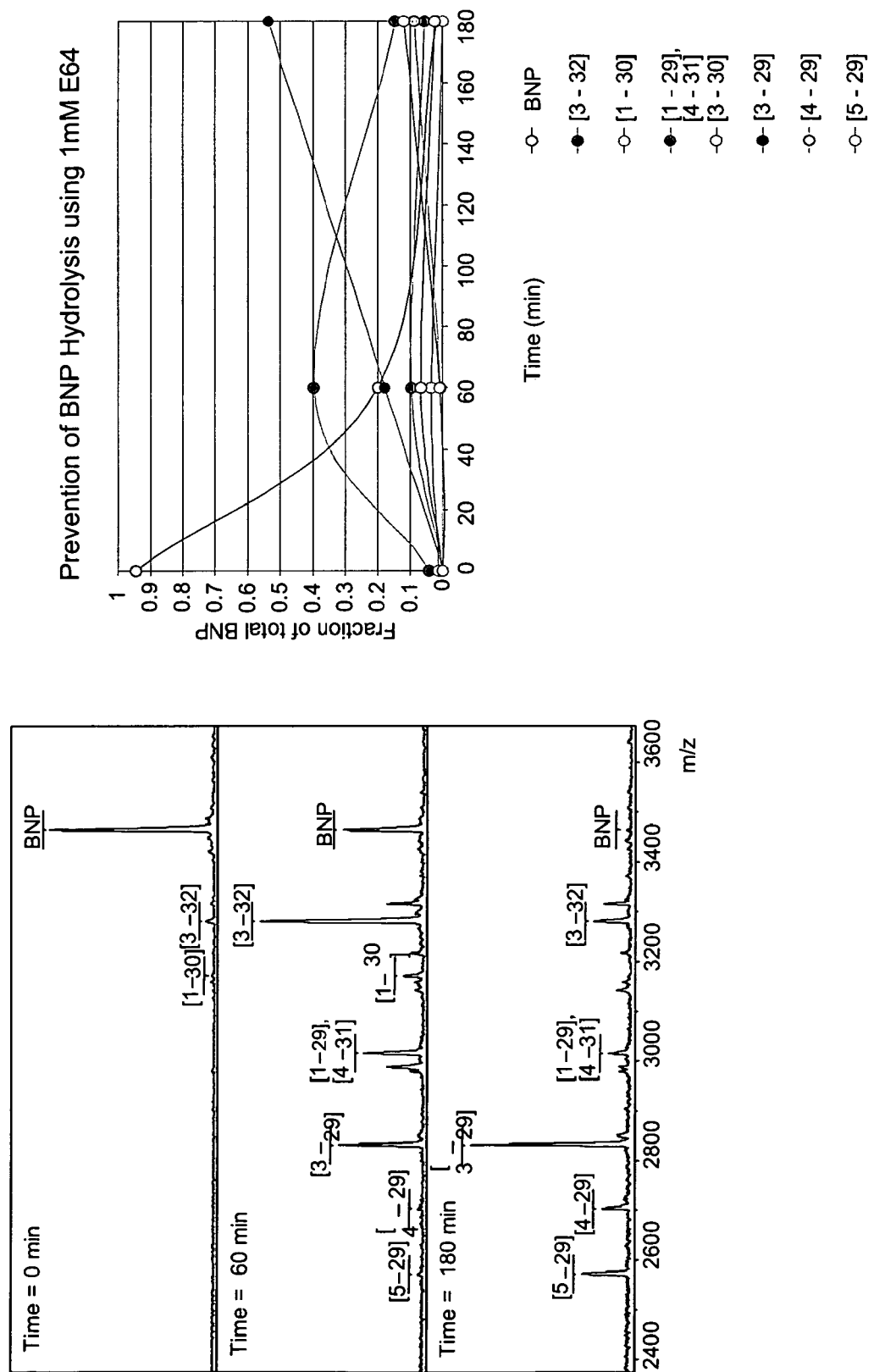
FIG. 7 shows BNP proteolysis in plasma treated with the protease inhibitor E64 (Calbiochem catalog no. 324890). The time course of both the mass spectra and the composition of BNP show little or no effect on BNP proteolysis.

E64 at 1 mM did not appreciably prevent the hydrolysis of BNP, as illustrated in FIG. 7.

Figure 8:
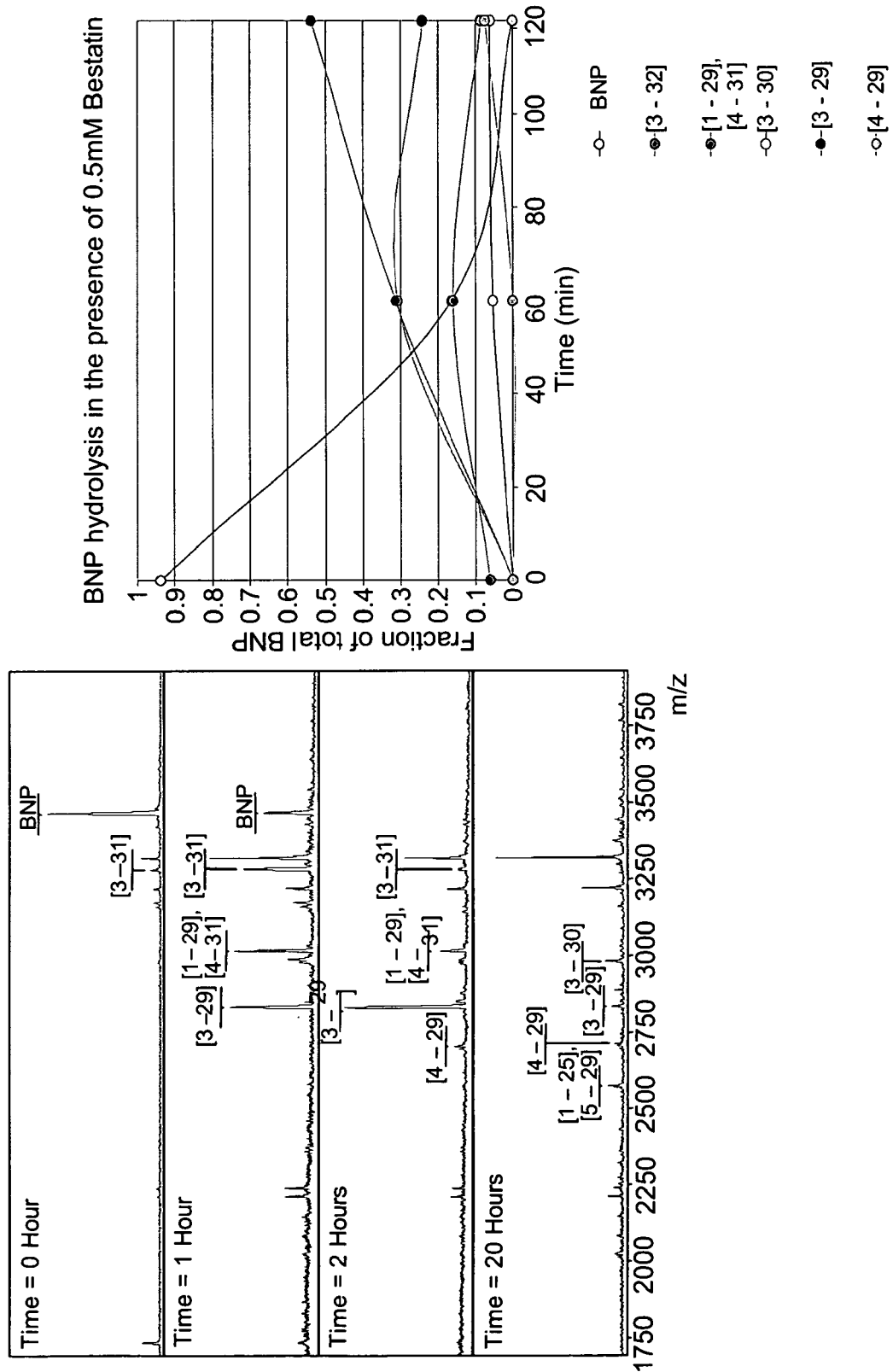
FIG. 8 shows BNP proteolysis in plasma treated with the protease inhibitor Bestatin (Calbiochem catalog no. 200484). The time course of both the mass spectra and the composition of BNP show that 0.5 mM Bestatin has little or no effect on BNP proteolysis.

Bestatin at 0.5 mM did not appreciably prevent the hydrolysis of BNP, as illustrated in FIG. 8.

Example 5

Further testing identified Leupeptin and AEBSF as possessing some inhibitory activity. Briefly, aliquots of heparin plasma were treated with each one of these protease inhibitors. To each aliquot of plasma, $BNP_{1-32}$ was added at 10 ng/mL and incubated at room temperature. Aliquots were sequentially removed and analyzed for BNP hydrolysis.

Figure 9:
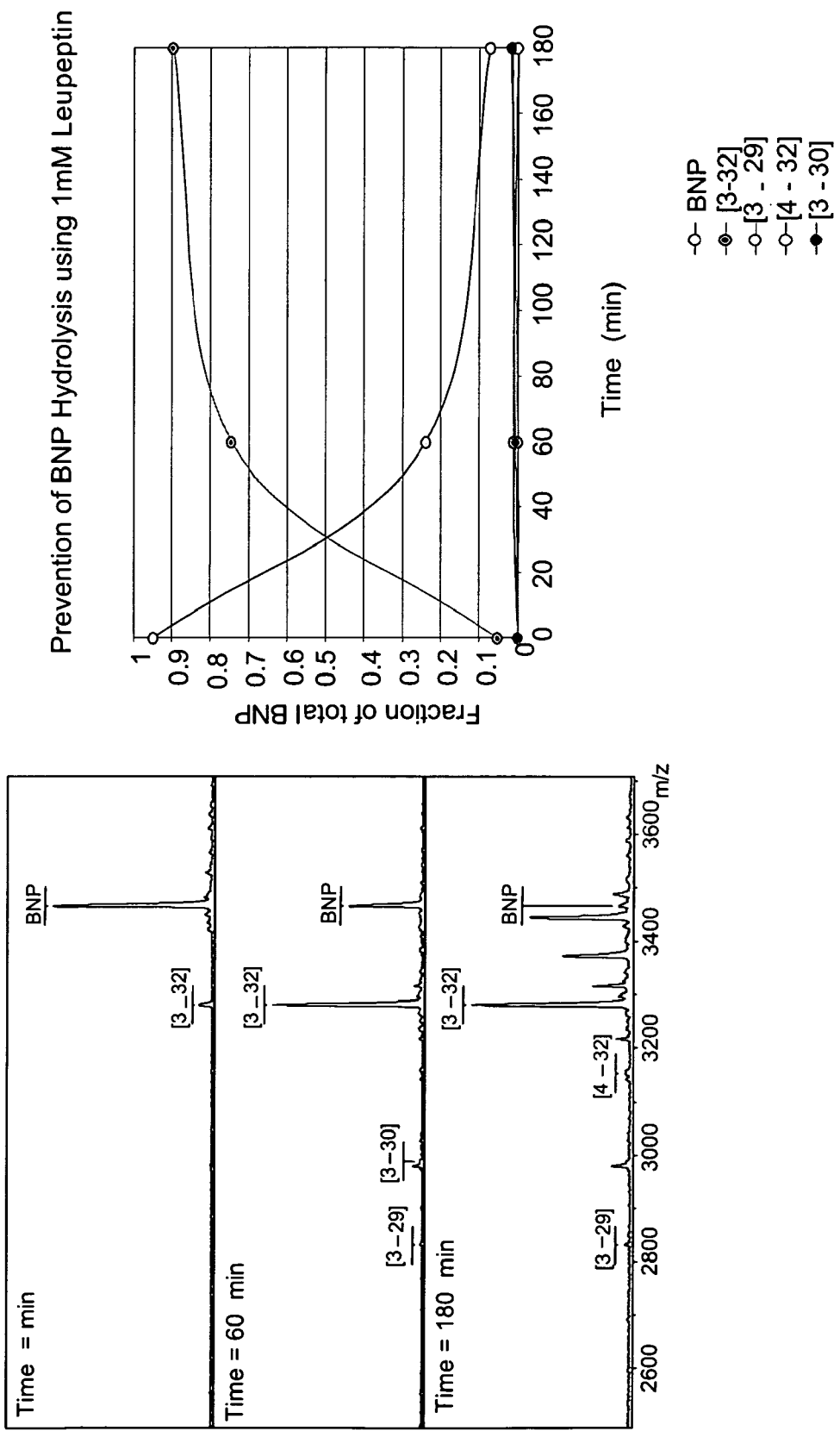
FIG. 9 shows BNP proteolysis in plasma treated with the protease inhibitor Leupeptin (Calbiochem catalog no. 108975). The time course of both the mass spectra and the composition of BNP show the ability of 1 mM Leupeptin slow BNP proteolysis.

Leupeptin at 0.1 mM slowed the hydrolysis of BNP, as illustrated in FIG. 9.

Figure 10:
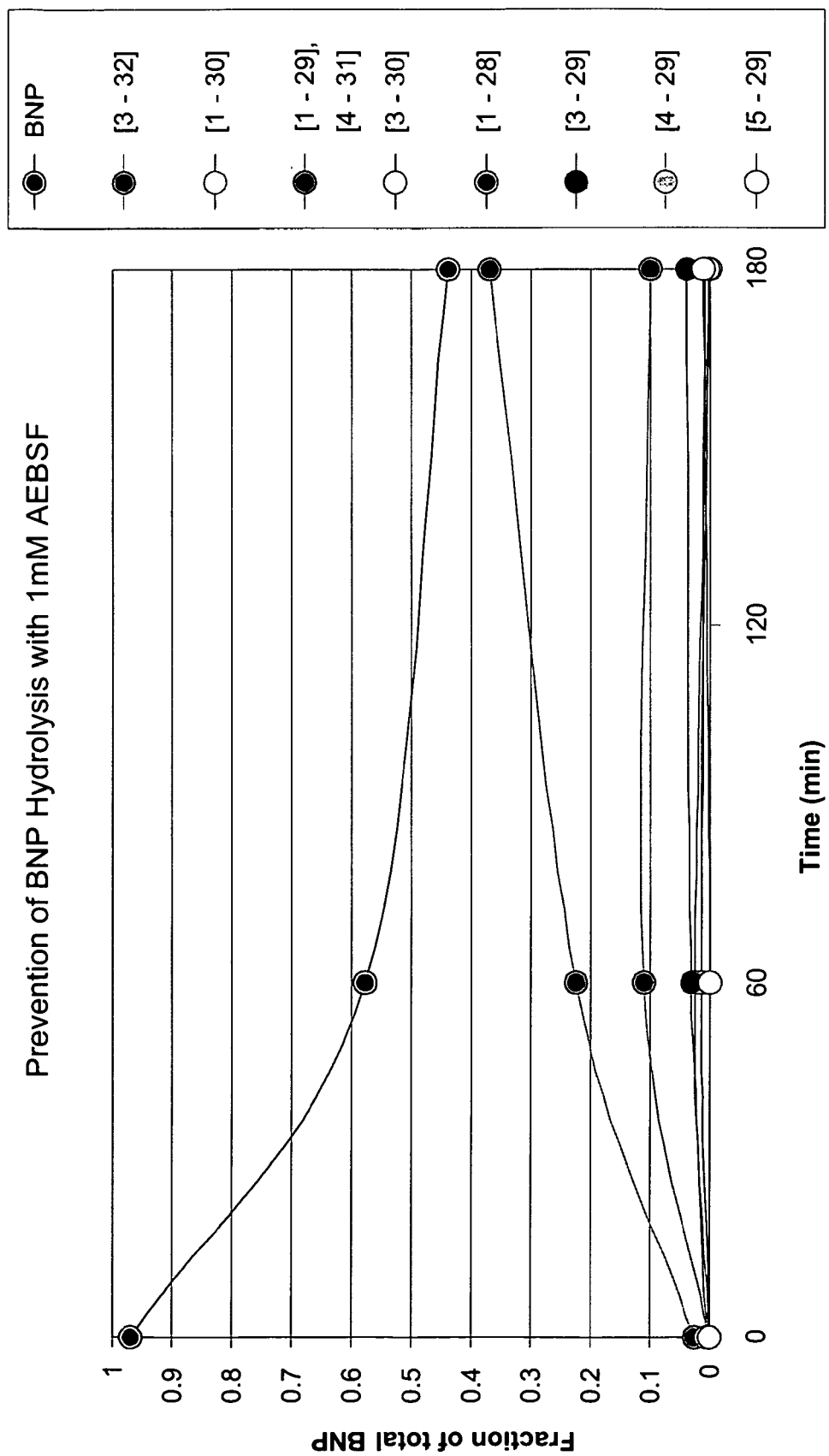
FIG. 10 shows reduced BNP proteolysis in plasma treated with the protease inhibitor AEBSF at 1 mM for up to 3 hours.

AEBSF at 1 mM slowed the hydrolysis of BNP as is illustrated in FIG. 10.

Figure 11:
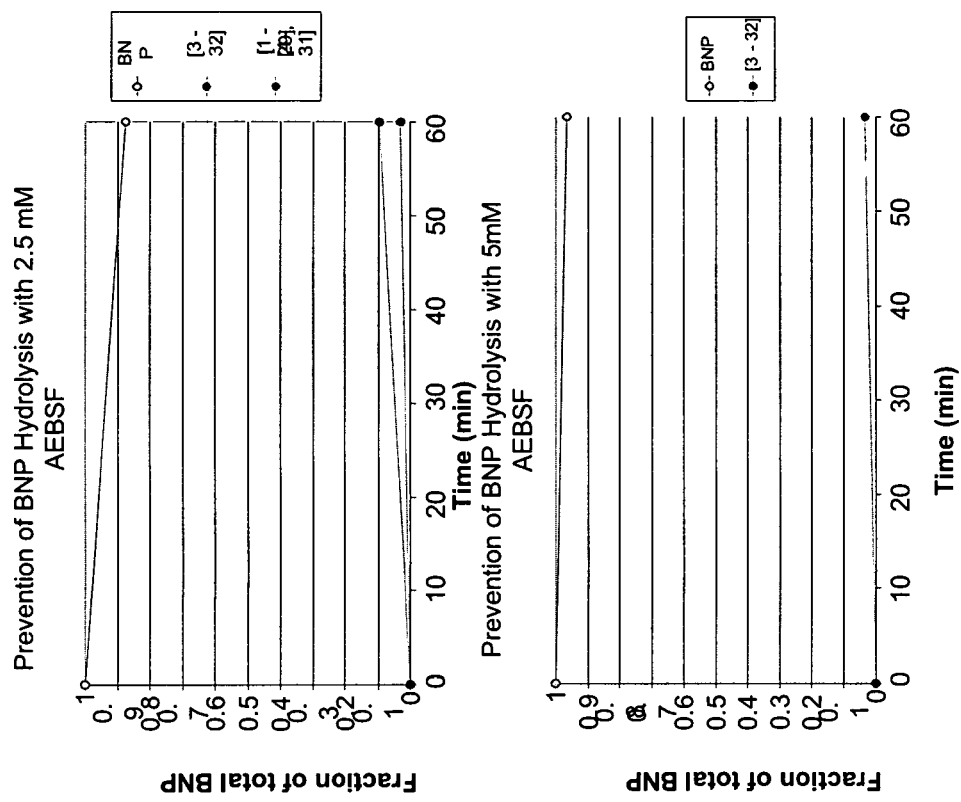
FIG. 11 shows reduced BNP proteolysis in plasma treated with the protease inhibitor AEBSF at 2.5 mM or 5 mM.
Figure 11:
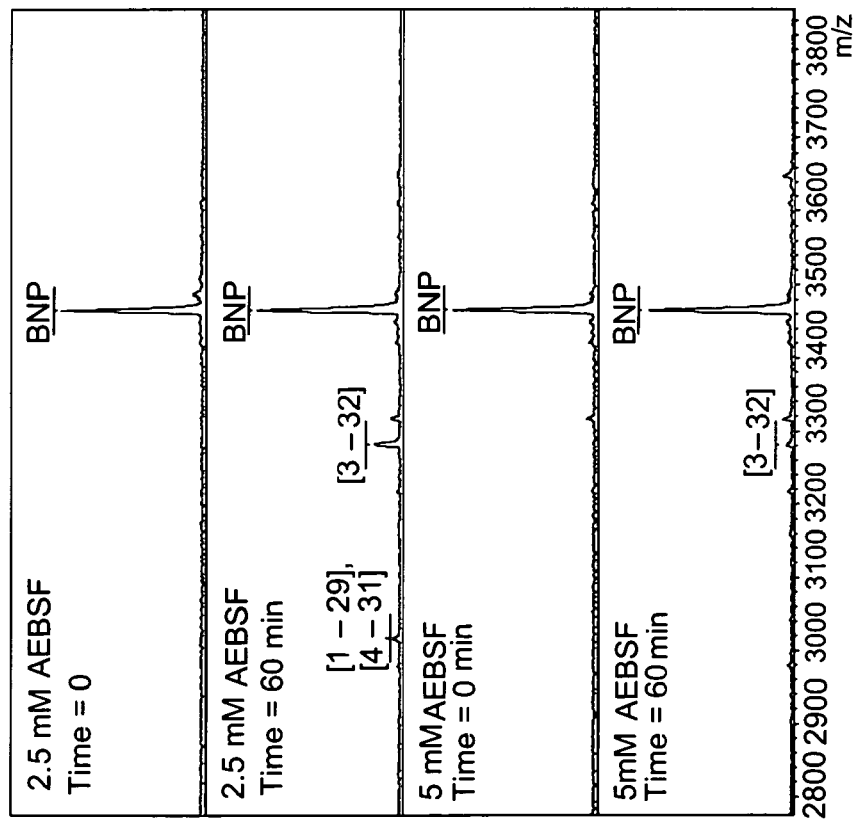

At a higher concentrations of 2.5 mM and 5 mM AEBSF almost completely inhibited the hydrolysis of BNP as is illustrated in FIG. 11, but at the same time it caused adduct formation, which is illustrated in FIG. 11.

Example 6

Further testing added to the list of inexpensive protease inhibitors effective in combination with AEBSF in avoiding adducts starting with benzamidine hydrochloride (Calbiochem catalog no. 199001). Benzamidine hydrochloride possesses inhibitory activity in its own right. Briefly, aliquots of heparin plasma were treated with the protease inhibitor. To each aliquot of plasma, $BNP_{1-32}$ was added at 10 ng/mL and incubated at room temperature. Aliquots were sequentially removed and analyzed for BNP hydrolysis.

Figure 12:
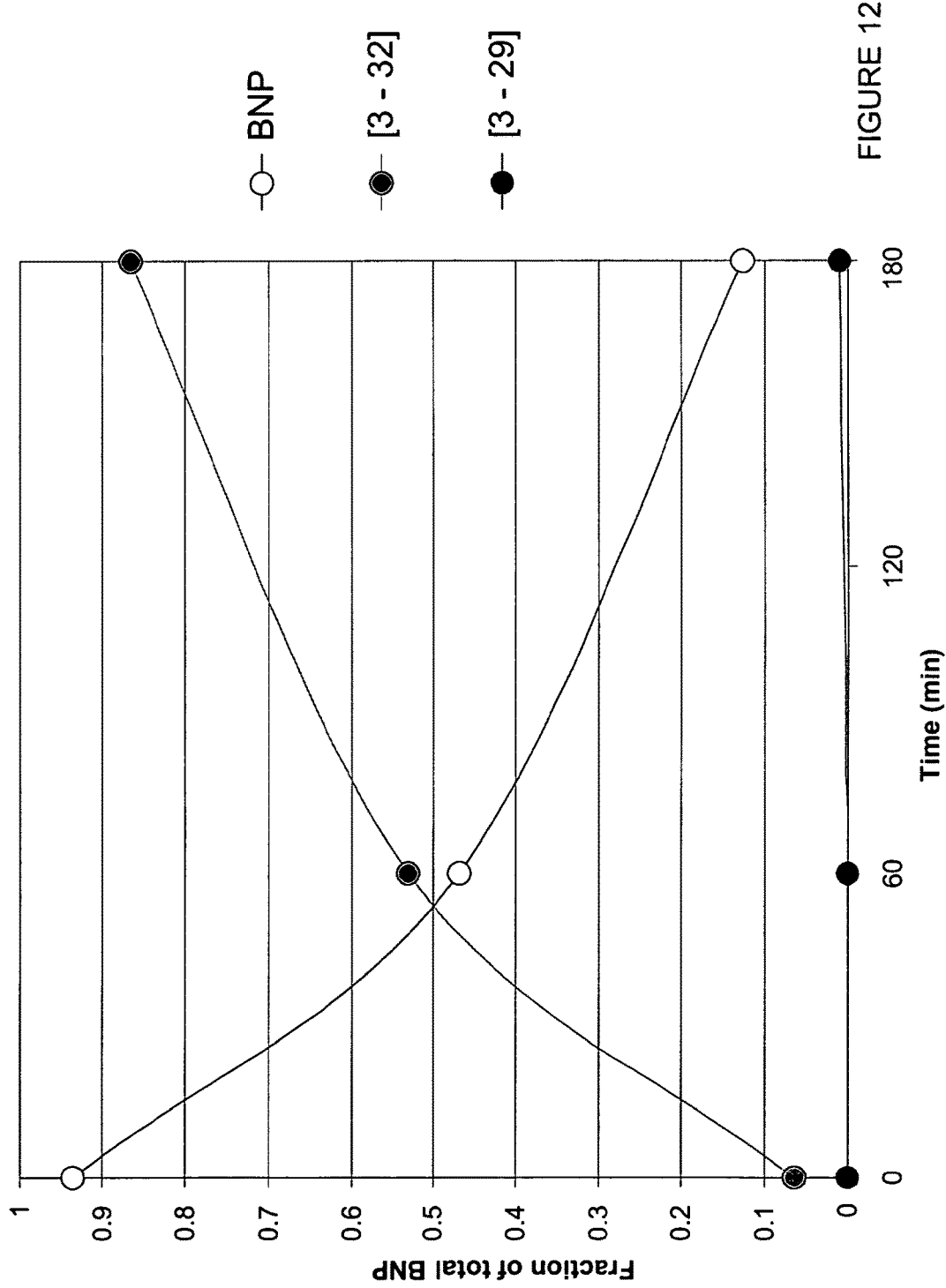
FIG. 12 shows reduced BNP proteolysis in plasma treated with the protease inhibitor PPACK I.
Figure 13:
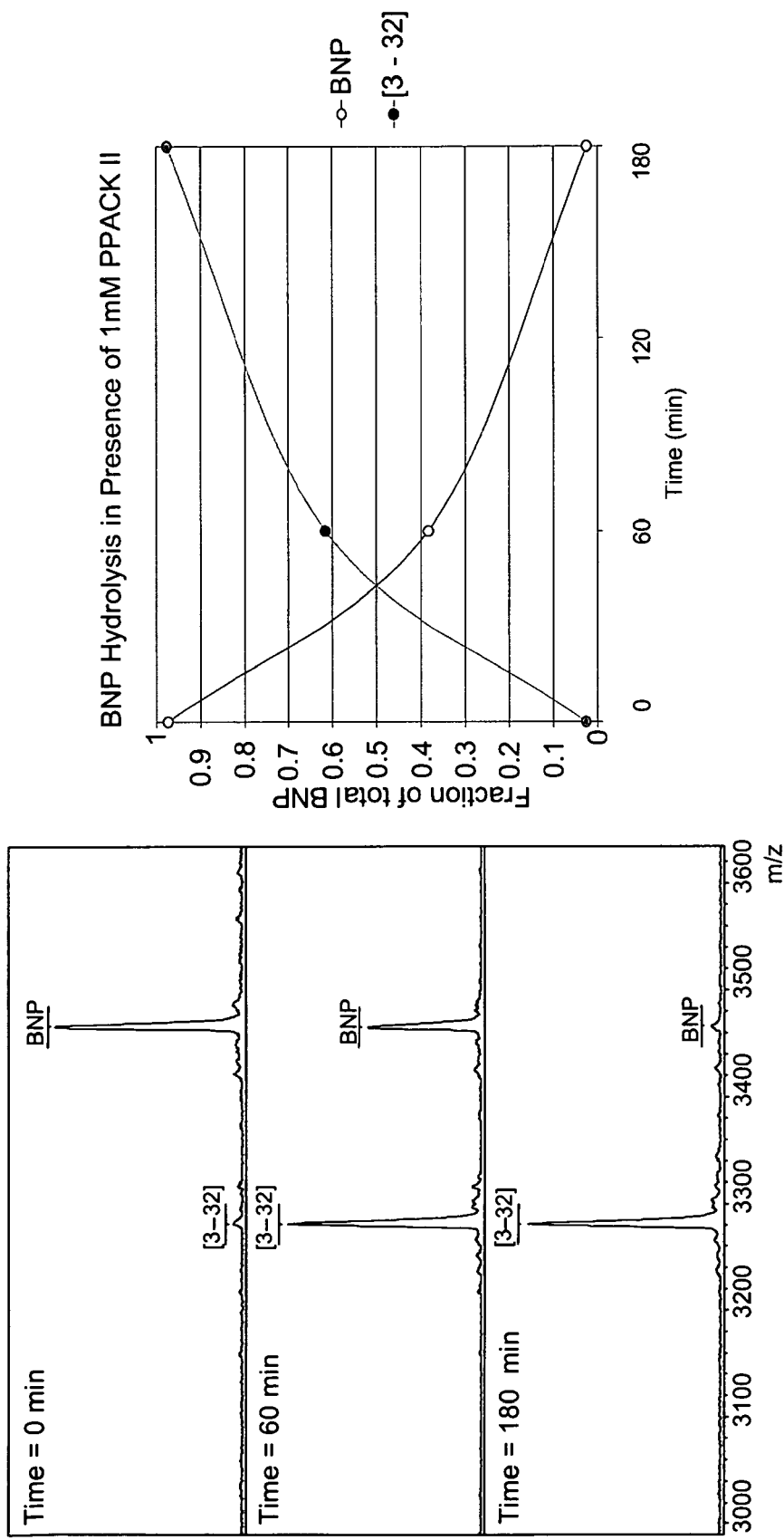
FIG. 13 shows reduced BNP proteolysis in plasma treated with the protease inhibitor PPACK II.

In addition, PPACK I dihydrochloride (Calbiochem catalog no. 520222) and PPACK II trifluoroacetate salt (Calbiochem catalog no. 520219) were also tested at a concentration of 1 mM each. PPACK I and PPACK II slowed the rate of BNP hydrolysis as is illustrated in FIGS. 12 and 13 respectively.

Figure 14:
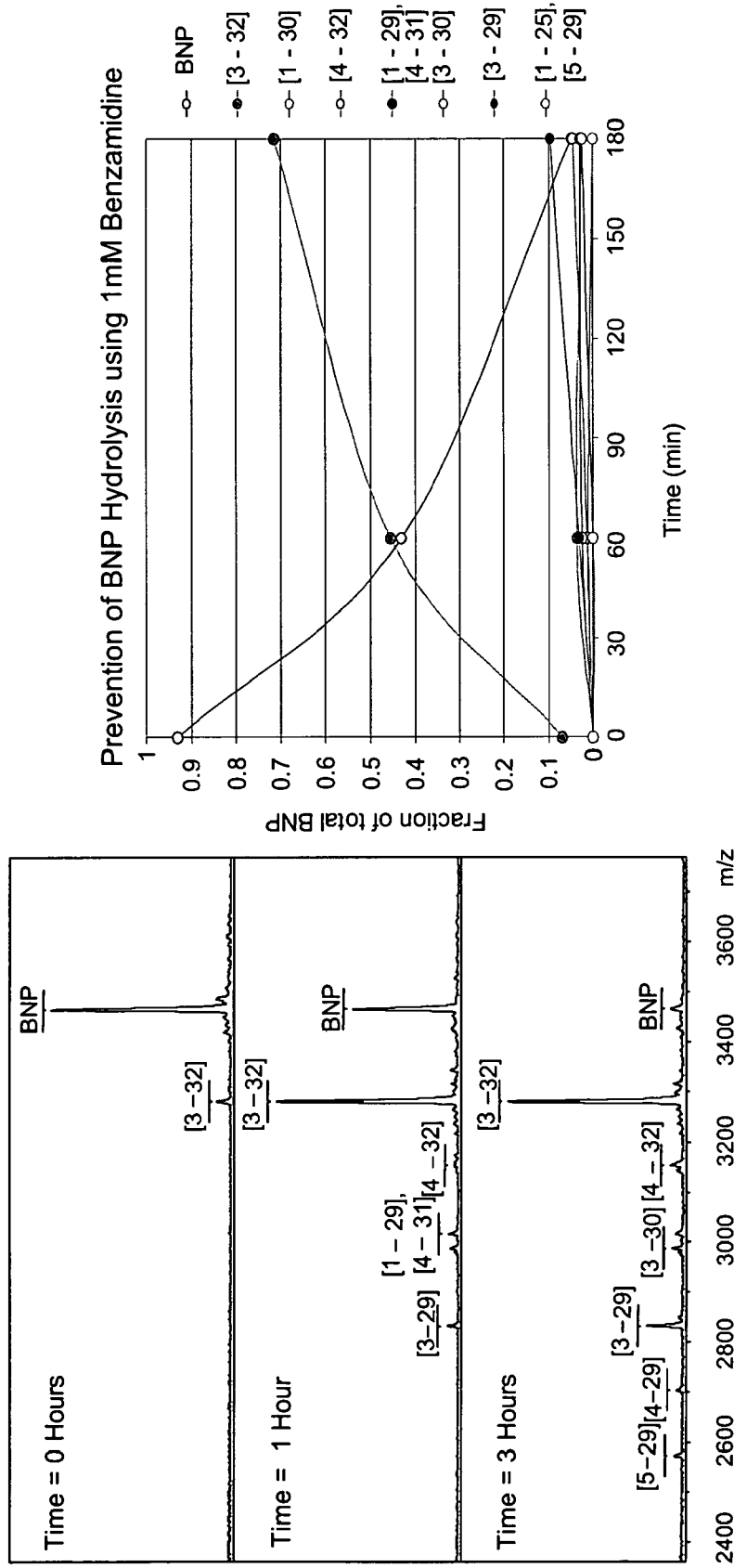
FIG. 14 shows reduced BNP proteolysis in plasma treated with the protease inhibitor Benzamidine at 1 mM.

Benzamidine hydrochloride at 1 mM slowed the hydrolysis of BNP as is shown in FIG. 14, and it did so better than PPACK I and PPACK II, but it was not as effective as AEBSF.

Example 7

Pairing individual protease inhibitors at appropriate concentrations avoided the formation of adducts to a significant degree. Protease inhibitors observed to have complimentary activity further improved the inhibitory activity of the combination in a synergistic manner upon pairing. Paired protease inhibitors were evaluated for their effectiveness in (i) preventing the hydrolysis of BNP from $BNP_{1-32}$ to a particular hydrolysis product (e.g. $BNP_{3-32}$), or, alternatively (ii) reducing the hydrolysis of BNP across the board.

Figure 15:
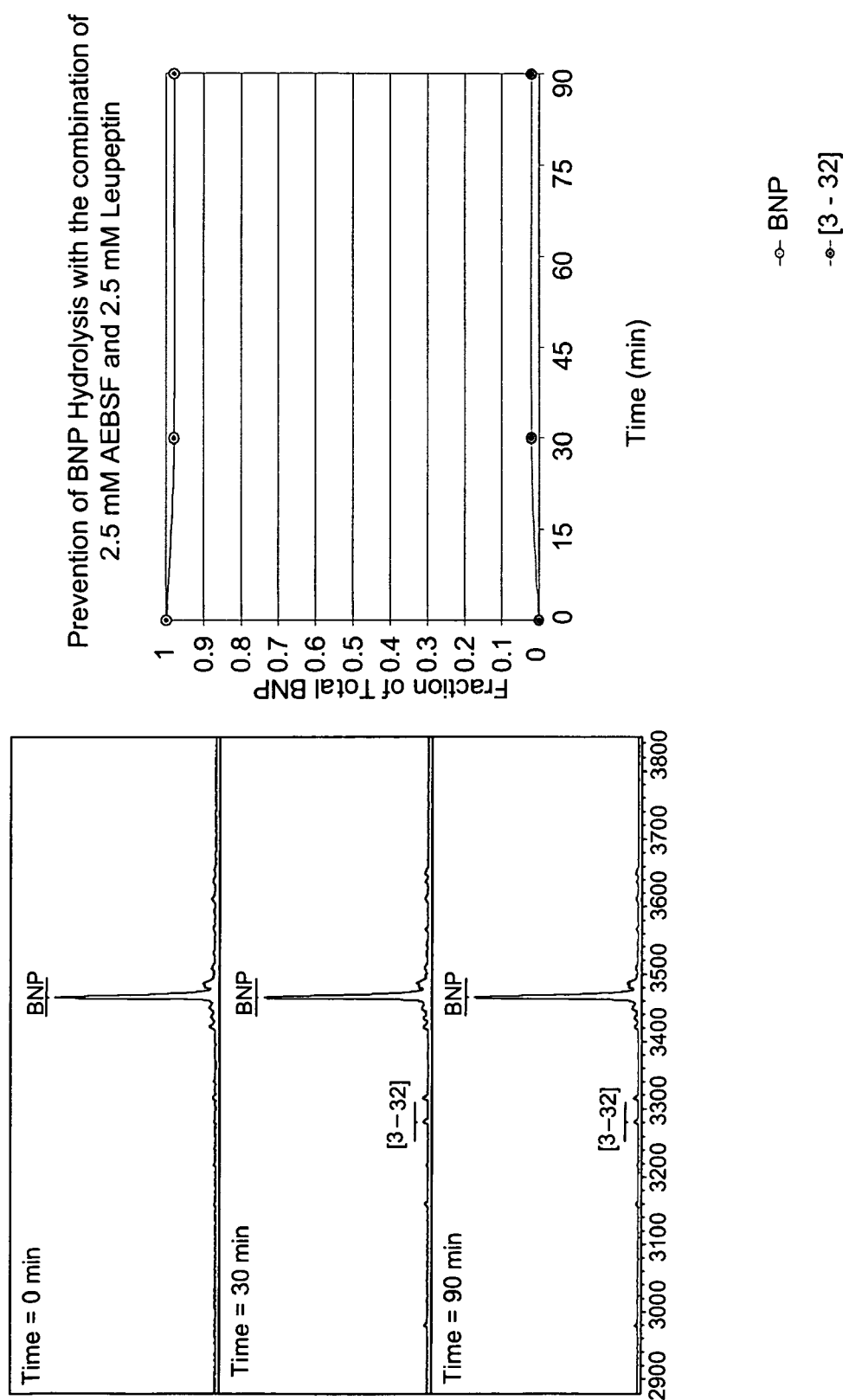
FIG. 15 shows almost complete inhibition of BNP proteolysis in plasma treated with a cocktail of protease inhibitors consisting of 2.5 mM AEBSF and 2.5 mM Leupeptin.

The cocktail of AEBSF and Leupeptin both at 2.5 mM concentrations significantly slowed to the point of almost eliminating detectable BNP hydrolysis as is illustrated in FIG. 15. As is seen, with the higher concentration of Leupeptin being used, the concentration of AEBSF could be lowered, although it still remained above the range recommended by ROCHE™ (see supra). Adduct formation was also eliminated by using Benzamidine at about 10-fold higher concentration with AEBSF.

Example 8

Although whole blood is obtained relatively easily and in principle is capable of providing valuable information, its use is limited by problems in handling it for use in reliable rapid diagnostic assays. For example, if a diagnostic assay is based on a colorimetric reaction, hemolysis of red blood cells introduces errors. Even when the readings are not affected by colors contributed by hemolysis, the very presence of cell lysates is a source of error because it results in variations in the volume of the recovered fluid fraction. It is therefore desirable to reproducibly separate cellular components of whole blood and generate a stable fluid fraction for downstream applications and testing.

Figure 16:
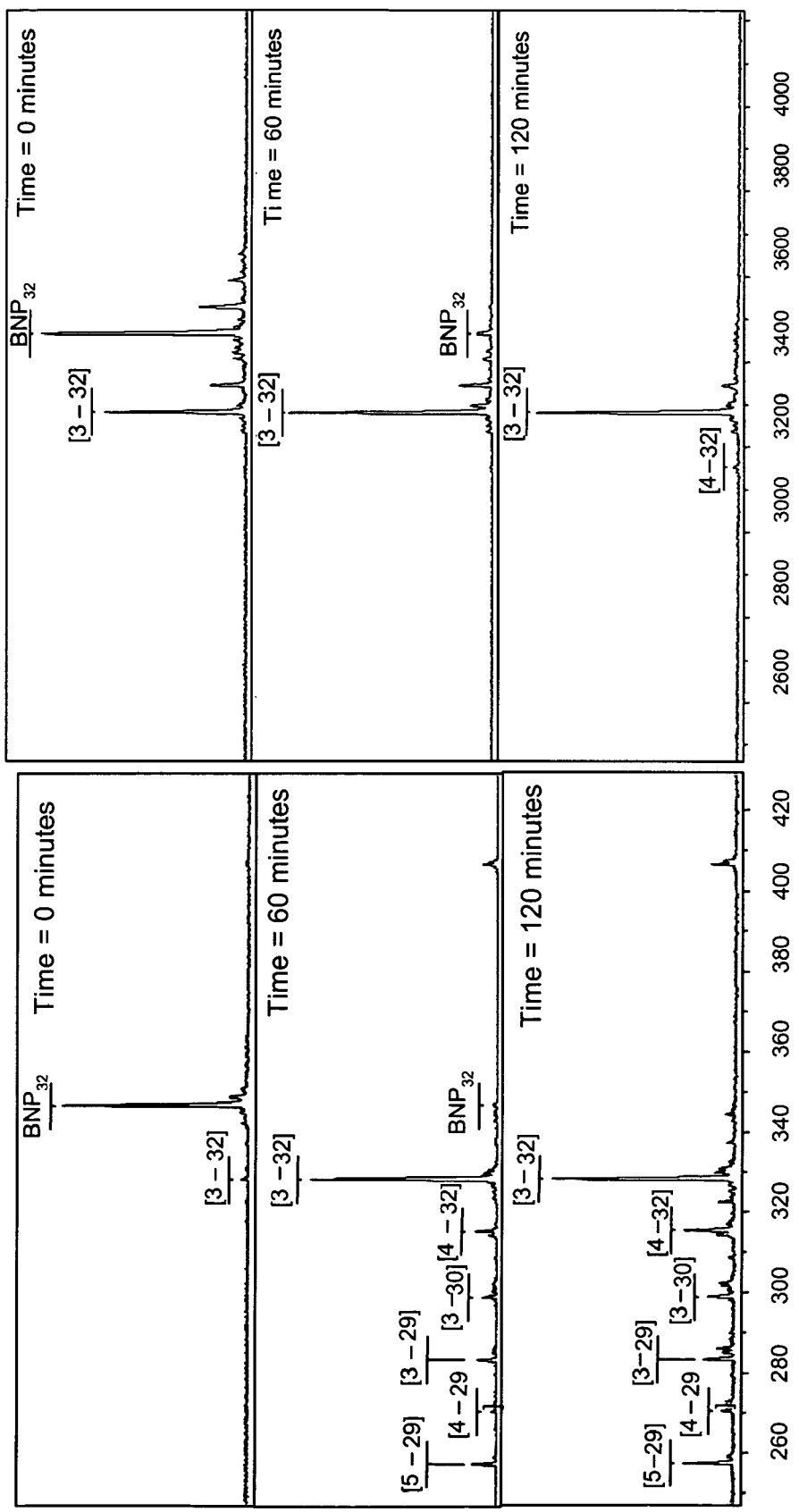
FIG. 16 shows BNP proteolysis in plasma from blood collected in heparin blood collection tubes (set of spectra on left) or in EDTA blood collection tubes (set of spectra at right). Collection tubes with EDTA reduce BNP hydrolysis leading to the formation of $BNP_{3-32}$.

Chelators are a preferred choice as blood anti-coagulants. Blood from a single individual was collected in both heparin and EDTA blood collection tubes. The collected blood was centrifuged to remove cellular components and the supernatant (plasma) was collected. To the EDTA and heparin plasma, BNPv was added and incubated at room temperature with aliquots removed for analysis of BNP hydrolysis at 1 hour and 2 hours. BNP hydrolysis shown in FIG. 16 illustrates the result of choosing EDTA or Heparin as the anti-coagulant agent. Heparin is relatively ineffective in preventing BNP proteolysis. In the presence of EDTA BNP hydrolysis stops with the formation of the $BNP_{3-32}$.

In addition to the need for preventing the hydrolysis BNP upon sample collection, it is also important to prevent the lysis of red blood cells during blood collection, which would otherwise release large amounts of cellular proteins/proteases. Therefore, blood collection with minimal cell lysis and little, if any coagulation, is preferable to avoid activating proteases by the very act of sampling.

Figure 17:
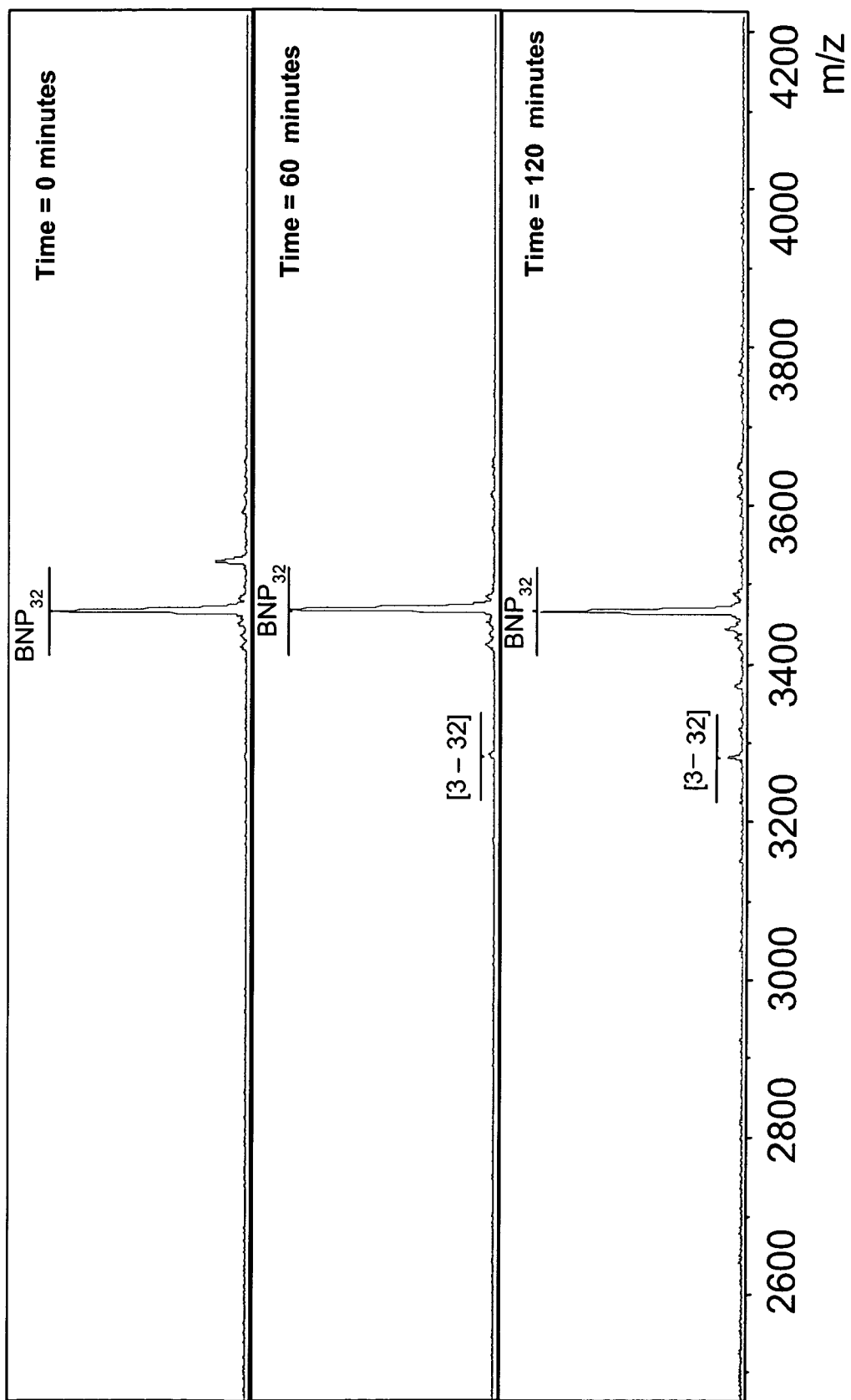
FIG. 17 shows prevention of BNP proteolysis in plasma from blood collected in EDTA tubes containing 10 mM AEBSF and 20 mM Benzamidine. The mass spectra demonstrate little change in the BNP profile over a 2-hour period of incubating the $BNP_{1-32}$.

Illustrative results from the use of EDTA or Heparin in collection tubes that also contain protease inhibitors are shown in FIG. 17 as reflected in the hydrolysis of BNP. BNP remains stable for at least 2 hours at room temperature when the blood is collected using the tubes containing EDTA and protease inhibitors AEBSF and Benzamindine.

Figure 18:
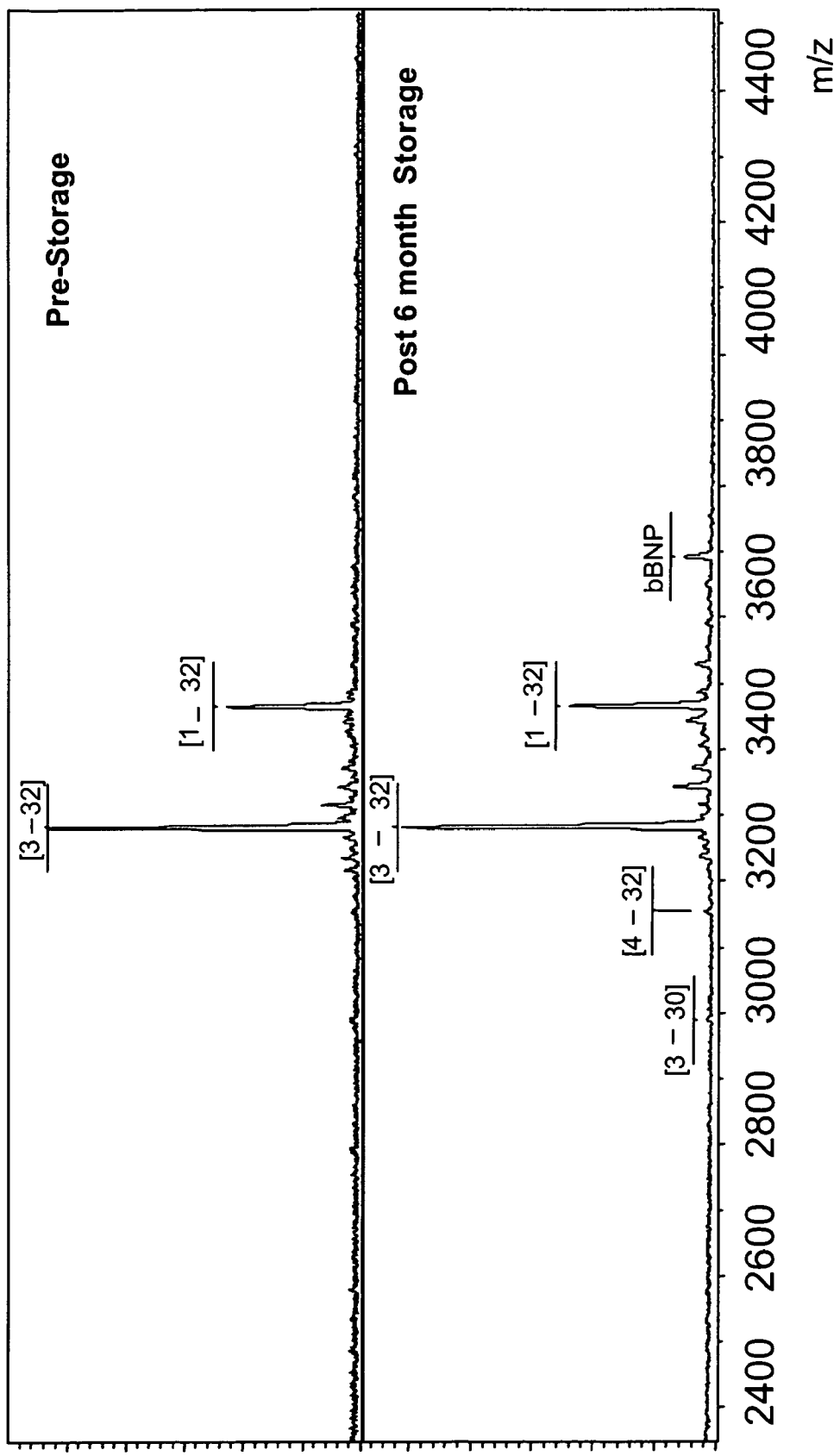
FIG. 18 shows BNP stability over a six-month period in plasma from blood collected using EDTA tubes. Protease inhibitors (10 mM AEBSF and 20 mM Benzamidine) were added subsequent to the collection of blood in an EDTA tube and after brief degradation of $BNP_{1-32}$ in blood. Plasma retrieved from the centrifugation of the whole blood was stored at −70° C. Aliquots of stored plasma were tested on the day of collection and six months later. Biotinylated BNP (bBNP) was added to serve as an internal reference in the aliquot tested six months later. Ratios between $BNP_{1-32}$ and $BNP_{3-32}$ are largely unchanged.
Figure 19:
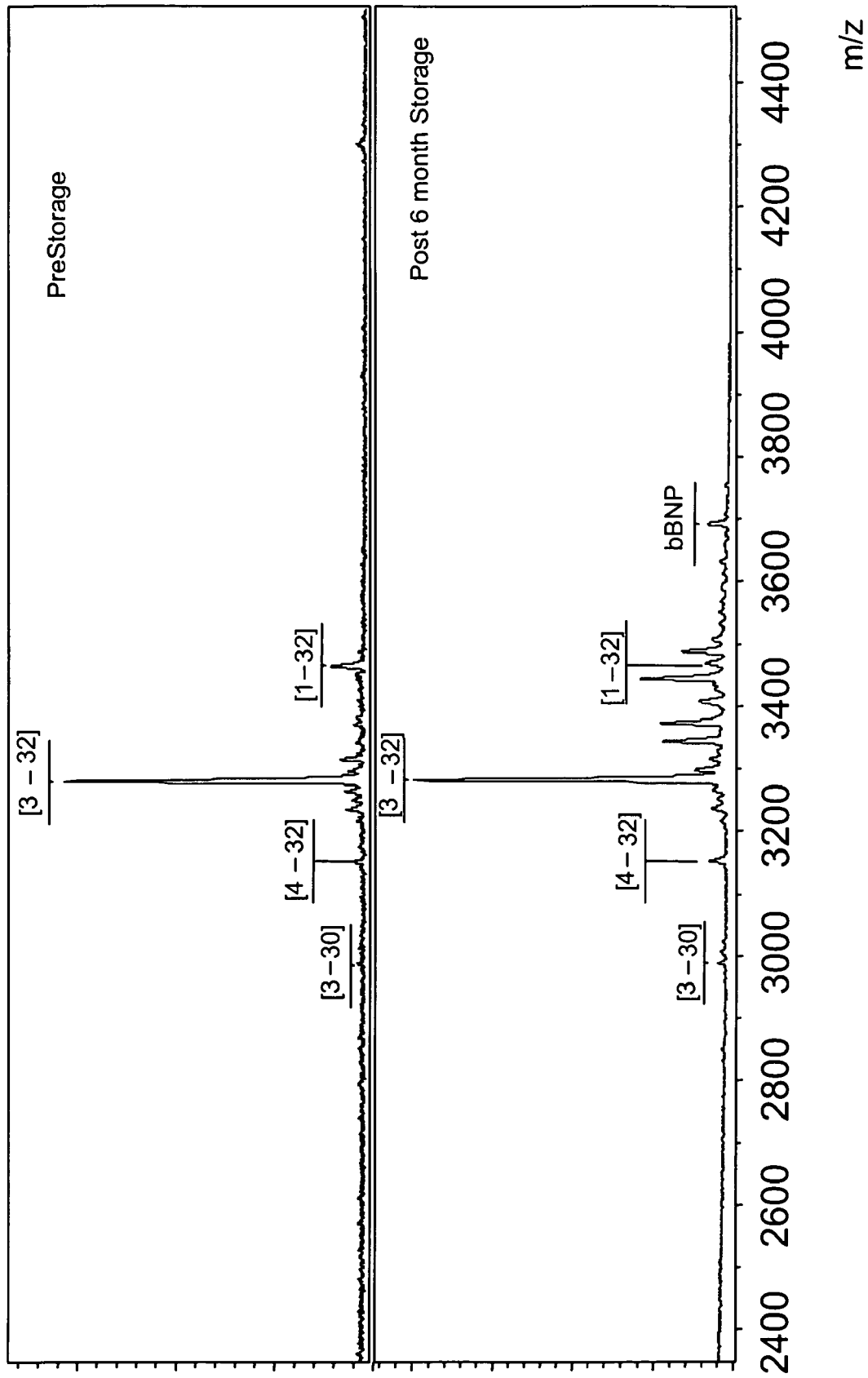
FIG. 19 shows BNP stability over a six-month period in plasma from blood collected in tubes containing EDTA. $BNP_{1-32}$ was added subsequent to the collection of blood and plasma retrieved from the centrifugation of the whole blood stored at −70° C. Aliquots of stored plasma were tested the day of collection and six months later. Added biotinylated BNP (bBNP) served as an internal reference in the aliquot tested six months later. Comparison of the ratio of the peak intensities of $BNP_{1-32}$ versus $BNP_{3-32}$ demonstrates the proteolysis of $BNP_{1-32}$ leading to the formation of $BNP_{3}$-32.

Further, plasma samples from blood sampled in tubes with EDTA followed with the addition of protease inhibitors are stable as measured by the hydrolysis of BNP over at least six months when stored at −70° C. as illustrated in FIG. 18. The limited proteolysis prior to the addition of the protease inhibitors is preserved in the sample. The sampled plasma was assayed for the presence of BNP fragments on the day of collection and then six month later. As is seen, the ratio of $BNP_{3-32}$ to $BNP_{1-32}$ is essentially unchanged demonstrating the stability of a sampled peptide profile over several months duration. Hydrolysis of BNP in heparin plasma is observed to progress towards the production of BNP hydrolysis products smaller than the $BNP_{3-32}$, as shown in FIG. 16, while in the EDTA plasma the hydrolysis stops at the formation of the $BNP_{3-32}$ as is shown in FIG. 19. This may reflect the presence of metalloproteinases in heparinized blood.

Hence, preferred blood collection tubes used for the collection of plasma samples for BNP analysis are EDTA blood collection tubes containing about 10 mM AEBSF and 20 mM Benzamidine.

Example 9

The effectiveness in preserving a sampled profile of interest by the disclosed approach is illustrated by examining the effect of possible proteases on BNP fragments. Although the proteases responsible for the hydrolysis of BNP likely exist in collected samples, samples collected in tubes containing the disclosed composition of chelators and protease inhibitors do not continue to undergo further proteolysis as is seen by examining BNP fragments for further proteolysis.

Therefore, the disclosed method, compositions and devices prevent the further hydrolysis of BNP species created in vivo, thus freezing the sampled profile at the point of blood collection. This is demonstrated by studying the effect on some of the BNP hydrolysis products.

Figure 20:
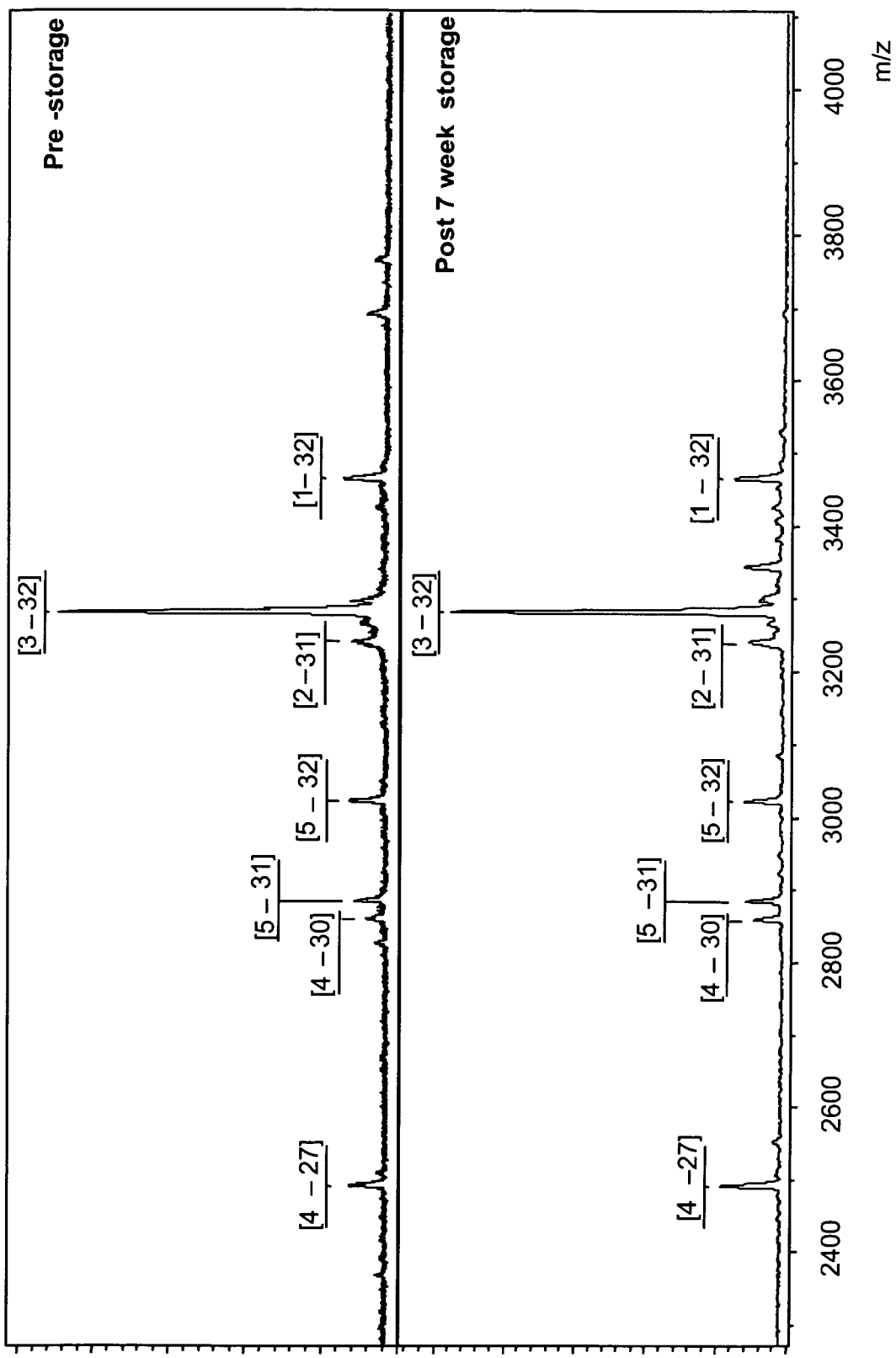
FIG. 20 shows the prevention of BNP hydrolysis in EDTA collection tubes containing 10 mM AEBSF and 20 mM Benzamidine. Blood was collected in EDTA tubes and treated with 10 mM AEBSF and 20 mM Benzamidine. Synthesized BNP peptides $BNP_{1-329}$, $BNP_{3-32}$, $BNP_2$-319, $BNP_{5-32}$, $BNP_{5-319}$, $BNP_{4-30}$, and $BNP_{4-27}$ were then added to the collected blood prior to the preparation of plasma. An aliquot was tested for stability of BNP peptides prior to storage and after storing the plasma for 7 weeks at −70° C. Comparison of ratios between BNP peptides before storage versus after 7 weeks of storage provides evidence of the stability of the BNP peptides in the presence of EDTA, 10 mM AEBSF and 20 mM Benzamidine.

To examine this, BNP peptides corresponding to those previously identified as products resulting from the hydrolysis of $BNP_{1-32}$ were synthesized and added to EDTA plasma treated with 10 mM AEBSF and 20 mM Benzamidine. An aliquot of the sample was analyzed for the added BNP peptides soon after the addition of the peptides to the plasma, while the rest of the plasma was stored at −70° C. for 7 weeks. After 7 weeks of storage the plasma was removed from the freezer, thawed and analyzed for the existence of the added BNP peptides. A comparison of the profile of BNP species from the two samples FIG. 20, shows that the ratios between the BNP peptides remain the same over the 7-week period.

Example 10

To further confirm the ability of the developed collection protocol to avert BNP hydrolysis and preserve the sample at the time of blood collection, Blood was collected from two consenting individuals, of which one was diagnosed with NYHA class IV heart failure while the other individual was determined to not exhibit HF. Blood samples from each were collected using the disclosed chelator-protease inhibitor blood collection tubes containing AEBSF and Benzamidine at levels high enough to provide concentrations in whole blood at 10 mM and 20 mM, respectively. Also added was a defined amount of biotinylated BNP to aid in quantitation by providing an internal control.

Figure 21:
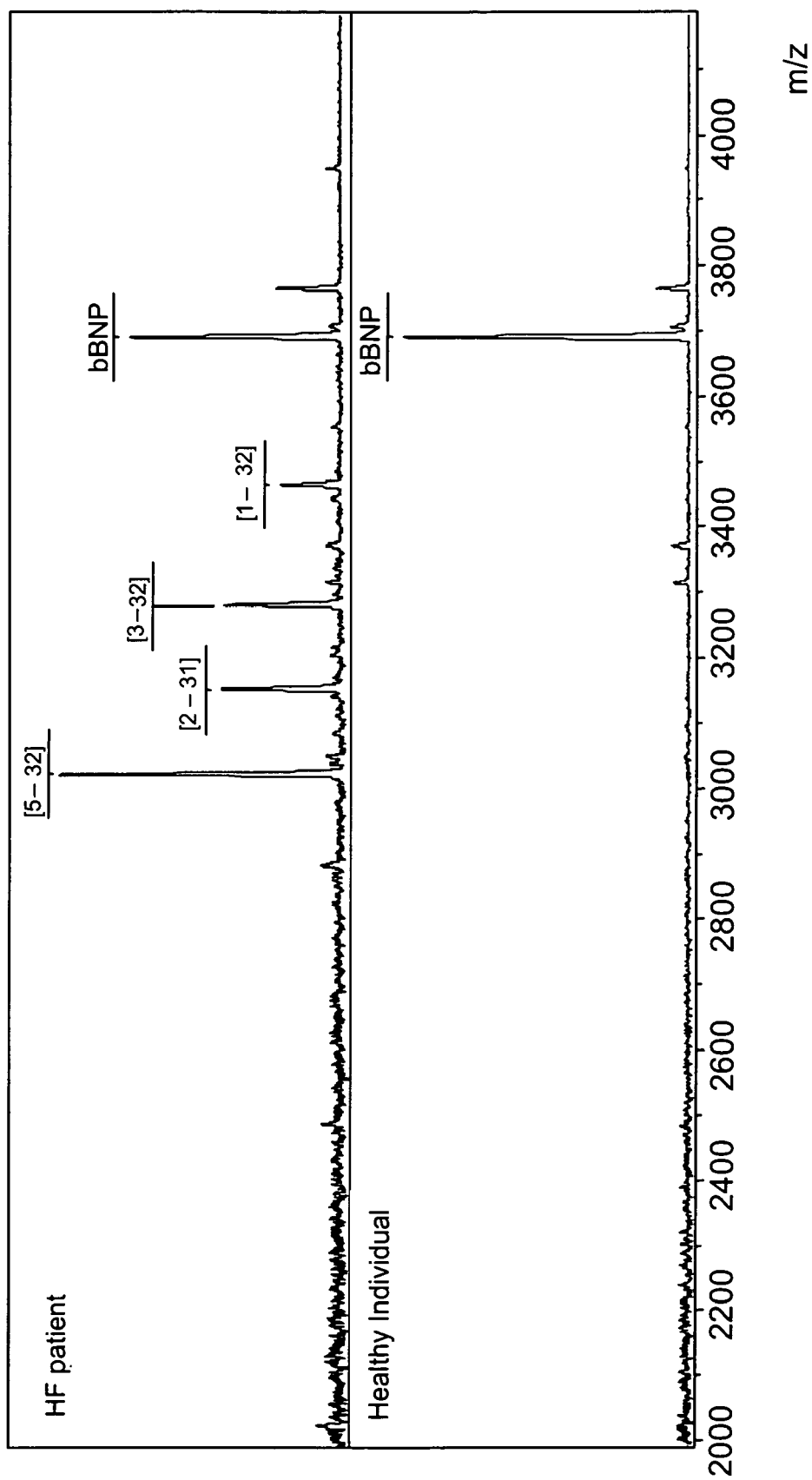
FIG. 21 shows a comparison of BNP stability in plasma from a HF patient (top) versus from a healthy individual (bottom) using the developed protocol for sample collection. Blood was collected from both a healthy and HF patient using the EDTA vacuum containers containing the protease inhibitors AEBSF and Benzamidine. The plasma collected from the blood samples was investigated for BNP using the BNP-specific MSIA.

Plasma from both individuals was analyzed for BNP related peptides. Illustrative results from this analysis are shown in FIG. 21. In comparison of the two mass spectra, one can easily identify the presence of the BNP species in the upper spectrum based upon the dominant peaks with intensities at a significant fraction of the internal reference (biotinylated BNP, bBNP) or greater. Based upon the mass, the peaks were identified as corresponding to $BNP_{1-32}$, $BNP_{3-32}$, $BNP_{2-31}$ and $BNP_{5-32}$.

Notably, as of present, there has been no known method for detecting the various BNP-related peptides separate from $BNP_{1-32}$. This provides evidence of the utility of the disclosed sampling method, composition and device for sampling a protein profile of interest at the time of blood collection. Preferably the profile is of peptides related to a natriuretic peptide.

Also disclosed herein are a number of devices or modification thereto to improve the sampling of blood and plasma. This is of particular interest in designing and deploying point-of-care devices to test for a peptide of interest. Preferably, the peptide is a natriuretic peptide or a precursor or fragment related thereto, such as BNP, pro-BNP or $BN_{1-76}$.

The ability to measure a wide variety of physiologically active substances, both naturally occurring and synthetic, has assumed increasing importance as an adjunct to both diagnosis and therapy. While for the most part such assays require clinical laboratory determinations, there is an increasing demand for point-of-care devices or even home testing. Depicted in FIG. 22 are schematic representations of some devices for collection of blood, preparation of a fluid fraction or for integrated assays for a substance of interest.

Figure 22:
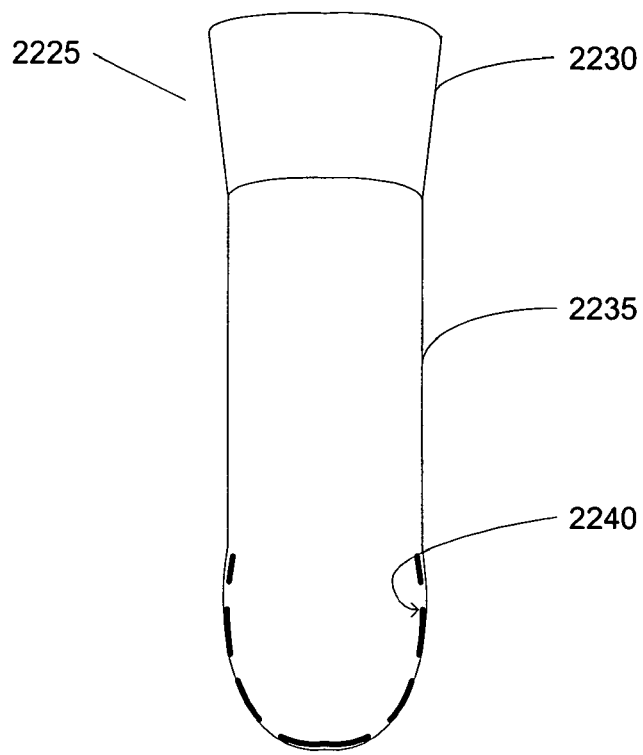
FIG. 22 shows two devices for sampling fluids with the aid of the disclosed compositions to reduce or eliminate modification of the sampled protein profile.
Figure 22:
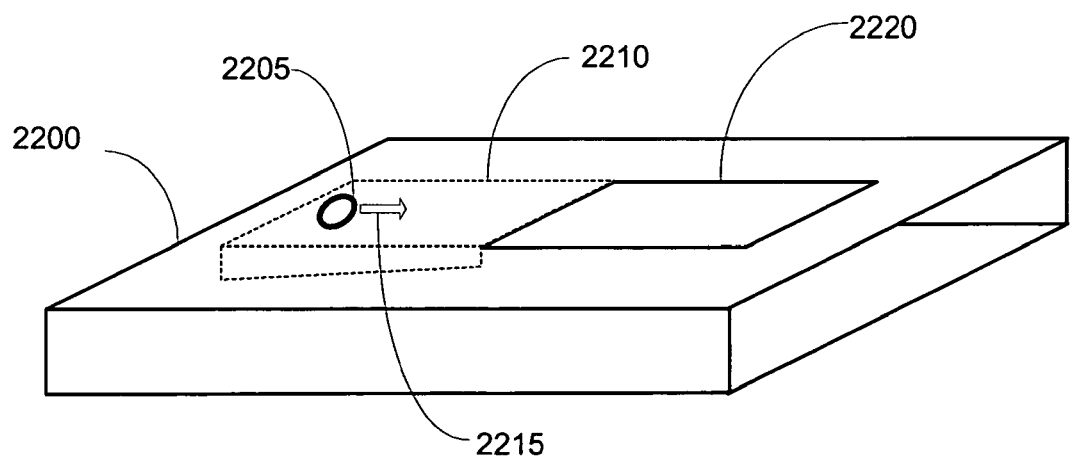

Schematically shown in FIG. 22, is a point-of-care device/component 2200, which has a port 2205 for receiving blood or another biological fluid. The applied fluid is filtered through a layer 2210, which is impregnated with the disclosed composition or a variant thereof. The fluid fraction flows as shown by arrow 2215 towards the portion 2220, which may be the analytical side of device 2200 or a reservoir for the separated fluid. This structure may be incorporated into a microfluidics device. Other variations include the use of the disclosed compositions in a liquid form and the use of additional ports in device 2200 to provide for washes and other steps.

Device 2225 is evacuated tube 2235 sealed by cap 2230, which is pierced to introduce a biological fluid. Alternatively, Device 2225 may just be a tube with cap 2230. Device 2225 is capable of holding a biological fluid sample with the proteolysis arrested as described herein due to the presence of disclosed composition 2240, preferably in a solid form. Disclosed composition 2240 may include stabilizers and buffering substances. Device 2225 is suitable for later laboratory analysis including tests for other substances such as glucose, metabolites or controlled substances in addition to preserving the protein profile of the sampled liquid.

It should be noted that the devices disclosed herein may include, with no loss of generality, additional protease inhibitors in combination with the disclosed composition. The composition is for use at a recommended final concentration, and accordingly markings may be provided for the final fluid level in a device similar to Device 2225. Further, composition 2240 in device 2225 may be a liquid, a powder or a lyophilized preparation. Some additional non-exhaustive description of devices modified by the use of the disclosed compositions follows.

In another preferred embodiment, the disclosed composition in a component of a dry chemical layer or a receiving layer anterior to it. By including the disclosed composition in the dry chemical layer or a layer anterior to it allows harvesting of a fluid fraction without changes in the protein profile due to proteolysis or adduct formation. Dry chemical layers may include analytes like conjugated antibodies. In one such device developed by EPOCAL™ a sample is applied to the sample receiving layer to form complexes that are retained in a detection zone. Detection is based on enzymatic activity of the retained complexes in a one-step immunoassay product platform or an immunochromatographic strip.

It is highly desirable that such devices are fast, reproducible, and easy to use with few or no complicated procedures. Further, the devices should produce results that are easy to readable, accurate with the devices themselves being capable of being manufactured in mass quantities at a low per unit cost.

Attempts have been made to develop rapid diagnostics for the direct use of whole blood. For example, test papers coated with semi-permeable membranes to prevent the contact of larger components of the sample to contact the test paper have been developed (see, e.g., U.S. Pat. No. 3,092,465). Another example is the use of swellable films into which only the dissolved components of the blood, but not the erythrocytes, can penetrate (see, e.g., Federal Republic of Germany Patent Specification No. 15 98 153). In accordance with this disclosure, such devices should be modified with the addition of disclosed protease inhibitor and chelator compositions into the relevant matrices such as the papers and gels.

A conventional manner of separating the fluid fraction from erythrocytes is centrifugation. However, especially in the case of using small amounts of sample, such as 50 microliters or even less than a few micro liters, this gives rise to problems and the separation of supernatant and precipitated cellular components. Further, conventional methods require more handling time by the doctor, nurse, technician, or tester. Such additional handling is generally undesirable for efficiency as well as hygienic reasons. Moreover, in some point-of-care situations, a centrifuge may not be available.

Some separators for separating a fluid fraction from blood cells in sampled blood are known in the art. See, e.g., U.S. Pat. Nos. 4,477,575 and 4,816,224, which disclose the use of glass fibers having density of 0.1 to 0.5 gm./ml with an average fiber diameter of 0.2 to 5 microns for separating the fluid fraction from blood. Indeed, it is possible now to assay fluid samples from blood samples of the order of a few tens of microliters.

Blood separation devices described in U.S. Pat. No. 5,135,719 include a glass microfiber filter or filters with agglutinin for separating cellular components, e.g., erythrocytes, from the fluid fraction of whole blood. Agglutinin promotes the aggregation of blood cells and thereby improves the filtration process. The driving force for the movement of plasma from the filter to a downstream application is capillary force provided by a tubular capillary.

Without intending to be bound by theory, it is believed that in view of the results disclosed herein, it is desirable to either impregnate or otherwise add the chelator-protease inhibitor composition disclosed herein to better preserve the peptide profile of interest, in particular that of natriuretic peptides like those related to BNP.

In addition to glass fiber filters, polysulfone resins and other fibers may be employed in blood separators. Polysulfone resins are extremely chemically resistant and also have some desirable mechanical properties. They, however, must be converted to a micro-porous structure, either in the form of a sheet stock or as fibers, which can be impregnated (or otherwise supplemented) with the chelator-protease inhibitor composition disclosed herein to better preserve the peptide profile of interest, in particular that of natriuretic peptides like those related to BNP.

Biological fluids like blisters fluid reflect the underlying plasma composition and thus often are suitable for assaying for peptide profiles of interest. In addition, saliva and tears as well as cerebrospinal fluid, seminal fluid, lymph, blood, serum, sweat, blister fluid, lung fluid, saliva, lacrimal gland secretion, or urine and the like can be assayed for the presence and level of a peptide of interest. In the case of saliva and tears, in a preferred embodiment, freshly induced secretions are sampled.

Fresh secretions are more likely to reflect the plasma composition and to be free of contamination as well as exhibit acceptable reproducibility. As an example, in a preferred embodiment, citric acid or citrate are used to induce salivary secretions on cue. Similarly, many known agents can induce tear secretion from the lacrimal gland without causing excessive discomfort to the subject. Further, it should be noted that while serum is not employed as the biological fluid in a preferred embodiment, it is possible to use serum with safeguards against proteolysis such as the use of specific inhibitors of metalloproteinases and rapid preparation of a serum fluid fraction, preferably without appreciable cell lysis.

The level of peptides and proteins in each fluid fraction so obtained depends on the manner in which the fluid is secreted or formed in the body. In most instances, the composition of the biological fluid is related to plasma with modifications due to filtration of proteins, secretion of proteins into the fluid and active transport to control the ionic composition. An example of an extensively modified version of plasma is urine, which is formed in the kidneys by first filtering out of proteins and other large blood constituents followed by re-absorption of most of the water and then of ions along with glucose and a few other constituents to form urine which is highly enriched in end-products that need to be excreted.

Once a fluid fraction is obtained, it can be assayed relatively rapidly or stored for subsequent assays. Such assays may include detection of peptide fragments of interest by initial separation from the fluid fraction with antibodies, followed by assaying for mass or mobility of the separated fragments. Some techniques of interest are electrophoresis, isoelectric focusing, mass spectrometry, and the like.

In addition, it is possible to characterize a fragment by means of a sandwich assay in which another antibody or molecule or complexes with affinity to the now relatively purified molecule are used to detect the specific peptide(s) of interest. Some methods of detection may include techniques such as magneto-acoustic detection, in which change in the frequency due to a change in bound mass is detected in a system that combines the purification step with the detection step. Alternatively chemiluminescence, fluorescence, or enzymatic end results may be used to quantitate a peptide of interest, including in a microfluidic implementation.

Also disclosed herein are methods for sampling a protein profile in a biological fluid of interest. In such a method, some preferred steps include adding an effective amount of metal chelator to a sample of the biological fluid, as well as adding an effective amount of a first protease inhibitor suitable for inactivating serine proteases; and adding an effective amount of a second protease inhibitor selected from the group consisting of a lysosomal protease inhibitor and an additional broad spectrum serine protease inhibitor, whereby the sampled protein profile is essentially unmodified by the formation of adducts.

Such a sample may be stored for at least six months at seventy degrees centigrade below zero or for at least two hours at room temperature.

The method may further include modifying diagnostic and blood/fluid sampling devices with the disclosed composition. The method may further include using the disclosed compositions in assaying for tissue samples, including those from a biopsy, such as that of kidney tissue. In the context of natriuretic peptides like BNP, a kidney biopsy may be used to estimate the level of cGMP, which is generated intracellularly due to the action of circulating ANP or BNP. In addition, the local level of natriuretic peptides, or receptors therefore, can be estimated and the responsiveness to natriuretic peptides also estimated to better understand kidney function.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A composition comprising a mixture of:
   (a) a first protease inhibitor selected from the group consisting of leupeptin and benzamidine;
   (b) a second protease inhibitor that is 4-(2-aminoethyl) benzenesulfonyl fluoride hydrochloride (AEBSF), wherein the second protease inhibitor does not inhibit formation of protein adducts in a peptide in the absence of the first protease inhibitor; and
   (c) a peptide;
   wherein an effective concentration of the first protease inhibitor and the second protease inhibitor is a concentration effective to inhibit proteolysis of the peptide while not inducing formation of adducts of the peptide when combined, and
   wherein the effective concentration comprises:
   (i) about 20 mM benzamidine and about 10 mM AEBSF, or
   (ii) about 2.5 mM leupeptin and about 2.5 mM AEBSF.

2. The composition according to claim 1, wherein the composition is stable for at least one of (i) two hours at room temperature, and (ii) at least six months at −70° C.

3. The composition according to claim 1, further comprising a chelator.

4. The composition according to claim 3, wherein the chelator is ethylenediaminetetraacetic acid.

5. The composition according to claim 4, wherein the ethylenediaminetetraacetic acid is present in the composition at a concentration of at least about 1 mM.

6. A device comprising a tube and a cap, wherein the device is capable of holding a biological fluid sample, wherein the device has disposed therein:
   (a) a first protease inhibitor selected from the group consisting of leupeptin and benzamidine; and
   (b) a second protease inhibitor that is 4-(2-aminoethyl) benzenesulfonyl fluoride hydrochloride (AEBSF);
   wherein the device has disposed therein sufficient protease inhibitor to be at a concentration of:
   (i) about 20 mM benzamidine and about 10 mM AEBSF, or
   (ii) about 2.5 mM leupeptin and about 2.5 mM AEBSF, when diluted by the biological fluid sample.

7. The device according to claim 6, further comprising at least one stabilizer or buffer.

8. The device according to claim 6, further comprising a chelator.

9. The device according to claim 8, wherein the chelator is ethylenediaminetetraacetic acid.

10. The device according to claim 6, further comprising heparin.

11. The device according to claim 6, wherein the device has disposed therein about 10 mM AEBSF and about 20 mM benzamidine.

12. The device according to claim 6, wherein the device has disposed therein about 2.5 mM leupeptin and about 2.5 mM AEBSF.

13. A blood collection tube capable of holding a blood sample, wherein the blood collection tube has disposed therein:
   (a) a first protease inhibitor selected from the group consisting of leupeptin and benzamidine; and
   (b) a second protease inhibitor that is 4-(2-aminoethyl) benzenesulfonyl fluoride hydrochloride (AEBSF);
   wherein the blood collection tube has disposed therein sufficient protease inhibitor to be at a concentration of:
   (i) about 20 mM benzamidine and about 10 mM AEBSF, or
   (ii) about 2.5 mM leupeptin and about 2.5 mM AEBSF, when diluted by the blood sample.

14. The blood collection tube according to claim 13, further comprising at least one stabilizer or buffer.

15. The blood collection tube according to claim 13, further comprising a chelator.

16. The blood collection tube according to claim 13, wherein the chelator is ethylenediaminetetraacetic acid.

17. The blood collection tube according to claim 13, further comprising heparin.

18. The blood collection tube according to claim 13, wherein the blood collection tube has disposed therein about 10 mM AEBSF and about 20 mM benzamidine.

19. The blood collection tube according to claim 13, wherein the blood collection tube has disposed therein about 2.5 mM leupeptin and about 2.5 mM AEBSF.

* * * * *